(12) United States Patent
Mukoyama et al.

(10) Patent No.: US 10,767,173 B2
(45) Date of Patent: Sep. 8, 2020

(54) METHOD FOR CONVERTING GENOME SEQUENCE OF GRAM-POSITIVE BACTERIUM BY SPECIFICALLY CONVERTING NUCLEIC ACID BASE OF TARGETED DNA SEQUENCE, AND MOLECULAR COMPLEX USED IN SAME

(71) Applicants: NATIONAL UNIVERSITY CORPORATION KOBE UNIVERSITY, Kobe-shi, Hyogo (JP); NIPPON SHOKUBAI CO., LTD., Osaka-shi, Osaka (JP)

(72) Inventors: Masaharu Mukoyama, Tsukuba (JP); Eita Ichige, Tsukuba (JP); Keiji Nishida, Kobe (JP); Akihiko Kondo, Kobe (JP)

(73) Assignees: NATIONAL UNIVERSITY CORPORATION KOBE UNIVERSITY, Kobe (JP); NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/757,243

(22) PCT Filed: Sep. 9, 2016

(86) PCT No.: PCT/JP2016/076711
§ 371 (c)(1),
(2) Date: Mar. 2, 2018

(87) PCT Pub. No.: WO2017/043656
PCT Pub. Date: Mar. 16, 2017

(65) Prior Publication Data
US 2019/0203198 A1    Jul. 4, 2019

(30) Foreign Application Priority Data
Sep. 9, 2015  (JP) .................................. 2015-178022

(51) Int. Cl.
| | |
|---|---|
| *C12N 15/64* | (2006.01) |
| *C12N 15/66* | (2006.01) |
| *C12N 15/74* | (2006.01) |
| *C12N 15/10* | (2006.01) |
| *C12N 9/78* | (2006.01) |
| *C07K 14/245* | (2006.01) |
| *C12N 9/22* | (2006.01) |
| *C12N 15/09* | (2006.01) |
| *C07K 19/00* | (2006.01) |
| *C12N 1/20* | (2006.01) |

(52) U.S. Cl.
CPC .......... *C12N 15/102* (2013.01); *C07K 14/245* (2013.01); *C07K 19/00* (2013.01); *C12N 1/20* (2013.01); *C12N 9/22* (2013.01); *C12N 9/78* (2013.01); *C12N 15/09* (2013.01); *C12N 15/10* (2013.01); *C07K 2319/80* (2013.01); *C12N 2310/20* (2017.05); *C12Y 305/04005* (2013.01)

(58) Field of Classification Search
CPC ...... C12N 15/86; C12N 15/66; C12N 15/102; C12N 15/70
See application file for complete search history.

(56) References Cited

U.S. PATENT DOCUMENTS

| | | | |
|---|---|---|---|
| 8,697,359 | B1 | 4/2014 | Zhang |
| 2005/0208489 | A1 | 9/2005 | Carroll et al. |
| 2011/0002889 | A1 | 1/2011 | Barrangou et al. |
| 2011/0104787 | A1* | 5/2011 | Church .................... C12N 9/78 435/227 |
| 2011/0145940 | A1 | 6/2011 | Voytas et al. |
| 2014/0294773 | A1 | 10/2014 | Brouns et al. |
| 2014/0304853 | A1 | 10/2014 | Ainley et al. |

(Continued)

FOREIGN PATENT DOCUMENTS

| | | |
|---|---|---|
| CA | 2933625 A1 | 6/2015 |
| CN | 105934516 A | 9/2016 |

(Continued)

OTHER PUBLICATIONS

Conticello et al., "Evolution of the AID/APOBEC Family of Polynucleotide (Deoxy)cytidine Deaminases," *Mol. Biol. Evol.*, 22(2): 367-377 (2005).

(Continued)

*Primary Examiner* — Gary B Nickol
*Assistant Examiner* — Lakia J Jackson-Tongue
(74) *Attorney, Agent, or Firm* — Leydig, Voit & Mayer, Ltd.

(57) ABSTRACT

The invention provides a method of modifying a targeted site of gram-positive bacterium of a double stranded DNA. The method includes contacting the double-stranded DNA with a complex of a nucleic acid sequence-recognizing module that specifically binds to a target nucleotide sequence in a given double stranded DNA and a nucleic acid base converting enzyme to convert, delete, or insert one or more nucleotides in the targeted site without cleaving at least one strand of the double stranded DNA in the targeted site, by introducing the nucleic acid encoding the complex into the gram-positive bacterium. The invention also provide a nucleic acid-modifying enzyme complex of a nucleic acid sequence-recognizing module that specifically binds to a target nucleotide sequence in a double stranded DNA of a gram-positive bacterium and a nucleic acid base converting enzyme bonded to each other, which complex is used for the method.

12 Claims, 1 Drawing Sheet
Specification includes a Sequence Listing.

(56) References Cited

U.S. PATENT DOCUMENTS

| | | |
|---|---|---|
| 2014/0335521 A1 | 11/2014 | Nakamura et al. |
| 2014/0356867 A1 | 12/2014 | Peter et al. |
| 2015/0031134 A1 | 1/2015 | Zhang et al. |
| 2015/0166980 A1 | 6/2015 | Liu et al. |
| 2015/0232882 A1 | 8/2015 | Zhang et al. |
| 2015/0315576 A1 | 11/2015 | Caliando et al. |
| 2016/0200779 A1 | 7/2016 | Liu et al. |
| 2017/0073670 A1* | 3/2017 | Nishida ............... C12N 15/102 |
| 2017/0121693 A1 | 5/2017 | Liu et al. |
| 2017/0321210 A1 | 11/2017 | Nishida et al. |
| 2019/0024098 A1 | 1/2019 | Nishida et al. |
| 2019/0085342 A1* | 3/2019 | Nishida ................... C12N 9/10 |

FOREIGN PATENT DOCUMENTS

| | | |
|---|---|---|
| EP | 3115457 A1 | 1/2017 |
| EP | 3115457 A1 * | 11/2017 |
| JP | 2010-519929 A | 6/2010 |
| JP | 4968498 B2 | 7/2012 |
| JP | 2013-513389 A | 4/2013 |
| JP | 2013-128413 A | 7/2013 |
| JP | 2015-503535 A | 2/2015 |
| WO | WO 2010/132092 A2 | 11/2010 |
| WO | WO 2011/072246 A2 | 6/2011 |
| WO | WO 2013/058404 A1 | 4/2013 |
| WO | WO 2013/140250 A1 | 9/2013 |
| WO | WO 2013/176772 A1 | 11/2013 |
| WO | WO 2014/071235 A1 | 5/2014 |
| WO | WO 2014/093595 A1 | 6/2014 |
| WO | WO 2014/093712 A1 | 6/2014 |
| WO | WO 2015/035136 A2 | 3/2015 |
| WO | WO 2015/089406 A1 | 6/2015 |
| WO | WO 2015/133554 A1 | 9/2015 |
| WO | WO 2016/072399 A1 | 5/2016 |
| WO | WO 2017/070632 A2 | 4/2017 |
| WO | WO 2017/090761 A1 | 6/2017 |

OTHER PUBLICATIONS

Fang et al., "New Method of Genome Editing Derived From CRISPR/Cas9," Prog. Biochem. Biophys. 40(8): 691-702 (2013).
Finney-Manchester et al., "Harnessing mutagenic homologous recombination for targeted mutagenesis in vivo by TaGTEAM," Nucleic Acids Res., 41(9): e99 (2013).
Horvath et al., "CRISPR/Cas, the Immune System of Bacteria and Archaea," Science, 327: 167-170 (2010).
Kitamura et al., "Uracil DNA Glycosylase Counteracts APOBEC3G-Induced Hypermutation of Hepatitis B Viral Genomes: Excision Repair of Covalently Closed Circular DNA," PLoS Pathog., 9(5): e1003361 (2013).
Krokan et al., "Base Excision Repair," Cold Spring Harb. Perspect. Biol., 5(4): a012583 (2013).
Makarova et al., "Evolution and classification of the CRISPR-Cas systems," Nat. Rev. Microbiol., 9(6): 467-477 (2011).
O'Connell et al., "Programmable RNA recognition and cleavage by CRISPR/Cas9," Nature, 516(7530): 263-266 (2014).
Osakabe et al., "Genome Editing with Engineered Nucleases in Plants," Plant Cell Physiol., 56(3): 389-400 (2015).
Pingoud et al., "Type II restrictions endonucleases—a historical perspective and more," Nucleic Acids Res., 42(12): 7489-7527 (2014).
Ran et al., "Double Nicking by RNA-Guided CRISPR Cas9 for Enhanced Genome Editing Specificity," Cell, 154(6): 1380-1389 (2013).
Rittié et al., "Enzymes used in molecular biology: a useful guide," J. Cell. Commun. Signal., 2(1-2): 25-45 (2008).
Rogozin et al., "Evolution and diversification of lamprey antigen receptors: evidence for involvement of an AID-APOBEC family cytosine deaminase," Nat. Immunol., 8(6): 647-656 and Supplementary Table 1 (2007).
Shimatani et al., "Targeted base editing in rice and tomato using a CRISPR-Cas9 cytidine deaminase fusion," Nat. Biotechnol., 35(5): 441-443, Online Methods, and Corrigendum (2017).
Shmakov et al., "Discovery and Functional Characterization of Diverse Class 2 CRISPR-Cas Systems," Mol. Cell, 60(3): 385-397 (2015).
Szyf et al., "Maternal care, the epigenome and phenotypic differences in behavior," Reprod. Toxicol., 24(1): 9-19 (2007).
Xu et al., "Efficient Genome Editing in Clostridium cellulolyticum via CRISPR-Cas9 Nickase," Appl. Environ. Microbiol., 81(13): 4423-4431 and Supplementary Data (2015).
Zeng et al., "Highly efficient editing of the actinorhodin polyketide chain length factor gene in Streptomyces coelicolor M145 using CRISPR/Cas9-CodA(sm) combined system," Appl. Microbiol. Biotechnol., 99(24): 10575-10585 (2015).
Zetsche et al., "Cpf1 Is a Single RNA-Guided Endonuclease of a Class 2 CRISPR-Cas System," Cell, 163(3): 759-771 (2015).
Canadian Intellectual Property Office, Examination Report in Canadian Patent Application No. 2,947,941 (dated Jun. 22, 2018).
Chinese Patent Office, First Office Action in Chinese Patent Application No. 201580023875.6 (dated Sep. 3, 2018).
Japanese Patent Office, International Search Report in International Patent Application No. PCT/JP2016/076448 (dated Dec. 6, 2016).
Japanese Patent Office, International Search Report in International Patent Application No. PCT/JP2016/085075 (dated Feb. 21, 2017).
Japanese Patent Office, International Search Report in International Patent Application No. PCT/JP2017/016105 (dated Jul. 25, 2017).
Canadian Intellectual Property Offce, Examination Report in Canadian Patent Application No. 2,947,941 (dated Mar. 18, 2019).
European Patent Office, Communication Pursuant to Article 94(3) EPC in European Patent Application No. 15758734.6 (dated Apr. 4, 2019).
Char et al., "Heritable site-specific mutagenesis using TALENs in maize," Plant Biotechnol. J., 13(7): 1002-1010 (2015).
Kuscu et al., "CRISPR-Cas9-AID base editor is a powerful gain-of-function screening tool," Nat. Methods, 13(12): 983-984 (2016).
Ma et al., "Targeted AID-mediated mutagenesis (TAM) enables efficient genomic diversification in mammalian cells," Nat. Methods, 13(12): 1029-1035 and Online Methods (2016).
European Patent Office, Extended European Search Report in European Patent Application No. 17786061.6 (dated Sep. 4, 2019).
Bogdanove et al., "TAL Effectors: Customizable Proteins for DNA Targeting," Science, 333(6051): 1843-1846 (2011).
Cermak et al., "Efficient design and assembly of custom TALEN and other TAL effector-based constructs for DNA targeting," Nucleic Acids Research, 39(12): e82 (2011).
Cho et al., "Targeted genome engineering in human cells with the Cas9 RNA-guided endonuclease," Nat. Biotechnol., 31(3): 230-232 (2013).
Cong et al., "Multiplex Genome Engineering Using CRISPR/Cas Systems," Science, 339(6121): 819-823 (2013).
Dicarlo et al., "Genome engineering in Saccharomyces cerevisiae using CRISPR-Cas systems," Nucleic Acids Res., 41(7): 4336-4343 (2013).
Esvelt et al., "Genome-scale engineering for systems and synthetic biology," Molecular Systems Biology, 9: 641 (2013).
Gilbert et al., "CRISPR-Mediated Modular RNA-Guided Regulation of Transcription in Eukaryotes," Cell, 154(2): 442-451 (2013).
Jiang et al., "RNA-guided editing of bacterial genomes using CRISPR-Cas systems," Nat. Biotechnol., 31(3): 233-239 and online methods [2 pages] (2013).
Jinek et al., "A Programmable Dual-RNA-Guided DNA Endonuclease in Adaptive Bacterial Immunity," Science, 337(6096): 816-821 (2012).
Jinek et al., "RNA-programmed genome editing in human cells," eLIFE, 2: e00471 (2013).
Kim et al., "Genome-wide target specificities of CRISPR RNA-guided programmable deaminases," Nat. Biotechnol., 35(5): 475-480 (2017).
Komor et al., "Programmable editing of a target base in genomic DNA without double-stranded DNA cleavage," Nature, 533(7603): 420-424 (2016).

(56) References Cited

OTHER PUBLICATIONS

Lada et al., "AID/APOBEC cytosine deaminase induces genome-wide kataegis," *Biol. Direct*, 7: 47 (2012).
Lada et al., "Genome-Wide Mutation Avalanches Induced in Diploid Yeast Cells by a Base Analog or an APOBEC Deaminase," *PLoS Genet.*, 9(9): e1003736 (2013).
Mali et al., "Cas9 as a versatile tool for engineering biology," *Nature Methods*, 10(10): 957-963 (2013).
Mali et al., "RNA-Guided Human Genome Engineering via Cas9," *Science*: 339(6121): 823-826 (2013).
Mali et al., "CAS9 transcriptional activators for target specificity screening and paired nickases for cooperative genome engineering," *Nat. Biotechnol.*, 31(9): 833-838 and Supplemental Online Methods (2013).
Mussolino et al., "TALE nucleases: tailored genome engineering made easy," *Current Opinion in Biotechnology*, 23(5): 644-650 (2012).
Nishida et al., "Targeted nucleotide editing using hybrid prokaryotic and vertebrate adaptive immune systems," *Science*, 353(6305): aaf8729 (2016).
Perez-Pinera et al., "RNA-guided gene activation by CRISPR-Cas9-based transcription factors," *Nat. Methods*, 10(10): 973-976 (2013).
Plosky, "CRISPR-Mediated Base Editing without DNA Double-Strand Breaks," *Mol. Cell.*, 62(4): 477-478 (2016).
Ran et al., "Genome engineering using the CRISPR-Cas9 system," *Nat. Protoc.*, 8(11): 2281-2308 (2013).
Shalem et al., "Genome-Scale CRISPR-Cas9 Knockout Screening in Human Cells," *Science*, 343(6166): 84-87 and Supplementary Materials (2014).
Canadian Intellectual Property Office, Official Action and Examination Search Report in Canadian Patent Application No. 2,947,941 (dated Dec. 15, 2017).
European Patent Office, Communication Pursuant to Article 94(3) EPC in European Patent Application No. 15758734.6 (dated May 4, 2018).
Japanese Patent Office, International Preliminary Report on Patentability in International Patent Application No. PCT/JP2015/056436 (dated May 10, 2016).
Japanese Patent Office, International Search Report in International Patent Application No. PCT/JP2015/056436 (dated Jun. 9, 2015).
Japanese Patent Office, International Search Report in International Patent Application No. PCT/JP2016/076711 (dated Nov. 29, 2016).
Japanese Patent Office, Official Action in Japanese Patent Application No. 2017-164703 (dated May 16, 2018).
Chinese Patent Office, Second Office Action in Chinese Patent Application No. 201580023875.6 (dated May 7, 2019).
Bortesi et al., "The CRISPR/Cas9 system for plant genome editing and beyond," *Biotechnol. Adv.*, 33(1): 41-52 (2015).
U.S. Appl. No. 15/124,021, filed Nov. 9, 2016.
U.S. Appl. No. 15/757,646, filed Mar. 5, 2018.
U.S. Appl. No. 15/779,120, filed May 25, 2018.
U.S. Appl. No. 16/094,587, filed Oct. 18, 2018.
Arazoe et al., "Targeted Nucleotide Editing Technologies for Microbial Metabolic Engineering," *Biotechnol. J.*, 13(9): e1700596 (2018).
Mitsunobu et al., "Beyond Native Cas9: Manipulating Genomic Information and Function," *Trends Biotechnol.*, 35(10): 983-996 (2017).

\* cited by examiner

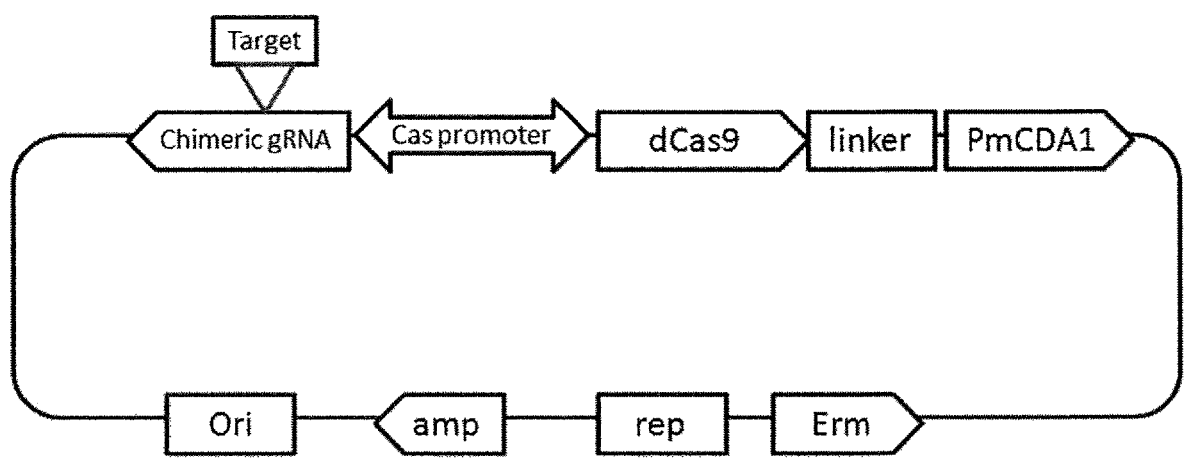

SEQUENCE LISTING

<160> NUMBER OF SEQ ID NOS: 75

<210> SEQ ID NO 1
<211> LENGTH: 83
<212> TYPE: DNA
<213> ORGANISM: Streptococcus pyogenes

<400> SEQUENCE: 1

```
gttttagagc tagaaatagc aagttaaaat aaggctagtc cgttatcaac ttgaaaaagt      60
ggcaccgagt cggtggtgct ttt                                              83
```

<210> SEQ ID NO 2
<211> LENGTH: 1002
<212> TYPE: DNA
<213> ORGANISM: Clostridium saccharoperbutylacetonicum
<220> FEATURE:
<221> NAME/KEY: CDS
<222> LOCATION: (1)..(1002)

<400> SEQUENCE: 2

```
atg gac ctt atg aaa aaa ata tgg gca gca gct caa tct gat aaa aga      48
Met Asp Leu Met Lys Lys Ile Trp Ala Ala Ala Gln Ser Asp Lys Arg
1               5                   10                  15 aga atc gtt ctt ccg gag gga aat gaa gaa aga aat att gag gct gca      96
Arg Ile Val Leu Pro Glu Gly Asn Glu Glu Arg Asn Ile Glu Ala Ala
                20                  25                  30 gga aaa ata caa gaa tta gga cta gca tat cca att tta att ggt ggg     144
Gly Lys Ile Gln Glu Leu Gly Leu Ala Tyr Pro Ile Leu Ile Gly Gly
            35                  40                  45 aaa gac gaa ata gaa gct aaa gca aag gaa ttg gat gta gac tta tct     192
Lys Asp Glu Ile Glu Ala Lys Ala Lys Glu Leu Asp Val Asp Leu Ser
        50                  55                  60 gga att gaa att ata gat cca gag aaa tcg gaa aac tta aac aag tat     240
Gly Ile Glu Ile Ile Asp Pro Glu Lys Ser Glu Asn Leu Asn Lys Tyr
65                  70                  75                  80 att aca gcc ttt tat gaa tta aga aaa agt aaa ggc gta act atg gaa     288
Ile Thr Ala Phe Tyr Glu Leu Arg Lys Ser Lys Gly Val Thr Met Glu
                85                  90                  95 aag gct gat aaa att gta aga gat cct cta tat ttc gct aca atg atg     336
Lys Ala Asp Lys Ile Val Arg Asp Pro Leu Tyr Phe Ala Thr Met Met
                100                 105                 110 gtt aaa cta gat gat gca gat gga atg gta tct gga gca gtt cat aca     384
Val Lys Leu Asp Asp Ala Asp Gly Met Val Ser Gly Ala Val His Thr
            115                 120                 125 act gga gat tta tta aga cca gga tta caa ata ata aag aca gca cca     432
Thr Gly Asp Leu Leu Arg Pro Gly Leu Gln Ile Ile Lys Thr Ala Pro
        130                 135                 140 ggt gta tct gta gtt tca agt ttc ttt ata atg caa gtg cca gga tct     480
Gly Val Ser Val Val Ser Ser Phe Phe Ile Met Gln Val Pro Gly Ser
```

```
                145                 150                 155                 160
act tat gga gaa caa gga act ctt ata ttc tct gac tgt gca gtt aac       528
Thr Tyr Gly Glu Gln Gly Thr Leu Ile Phe Ser Asp Cys Ala Val Asn
                    165                 170                 175 cca aat cca aat gaa gac caa tta gcc gct att gct att gca acg gct       576
Pro Asn Pro Asn Glu Asp Gln Leu Ala Ala Ile Ala Ile Ala Thr Ala
                180                 185                 190 gaa aca gca aag aga tta tgt aac atg gat cct aaa gta gca atg ctg       624
Glu Thr Ala Lys Arg Leu Cys Asn Met Asp Pro Lys Val Ala Met Leu
            195                 200                 205 tca ttc tcc aca atg gga agt gca gat aat gaa ttg gtt gat aaa gtt       672
Ser Phe Ser Thr Met Gly Ser Ala Asp Asn Glu Leu Val Asp Lys Val
        210                 215                 220 aga aat gca aca caa aaa gca aaa gaa atg aga cca gat tta gat att       720
Arg Asn Ala Thr Gln Lys Ala Lys Glu Met Arg Pro Asp Leu Asp Ile
225                 230                 235                 240 gat ggt gaa ctt caa tta gat gca gca att gtt aaa aaa gta gct gat       768
Asp Gly Glu Leu Gln Leu Asp Ala Ala Ile Val Lys Lys Val Ala Asp
                    245                 250                 255 caa aag gca cca aat agt aaa gta gca gga aaa gct aat gtt tta gta       816
Gln Lys Ala Pro Asn Ser Lys Val Ala Gly Lys Ala Asn Val Leu Val
                260                 265                 270 ttc cca gat tta caa gct gga aac ata ggt tat aaa tta gtc caa aga       864
Phe Pro Asp Leu Gln Ala Gly Asn Ile Gly Tyr Lys Leu Val Gln Arg
            275                 280                 285 ttt gca aat gca gaa gct att ggg cct att tgt caa ggc ttt gat aaa       912
Phe Ala Asn Ala Glu Ala Ile Gly Pro Ile Cys Gln Gly Phe Asp Lys
        290                 295                 300 cca ata aat gat tta tca aga gga tgt agt tca gat gat atc gta aat       960
Pro Ile Asn Asp Leu Ser Arg Gly Cys Ser Ser Asp Asp Ile Val Asn
305                 310                 315                 320 gtt gtt gca tta act gct gta caa gcg caa aac aat aaa tag              1002
Val Val Ala Leu Thr Ala Val Gln Ala Gln Asn Asn Lys
                    325                 330

<210> SEQ ID NO 3
<211> LENGTH: 333
<212> TYPE: PRT
<213> ORGANISM: Clostridium saccharoperbutylacetonicum

<400> SEQUENCE: 3

Met Asp Leu Met Lys Lys Ile Trp Ala Ala Gln Ser Asp Lys Arg
1               5                   10                  15

Arg Ile Val Leu Pro Glu Gly Asn Glu Glu Arg Asn Ile Glu Ala Ala
                20                  25                  30

Gly Lys Ile Gln Glu Leu Gly Leu Ala Tyr Pro Ile Leu Ile Gly Gly
            35                  40                  45

Lys Asp Glu Ile Glu Ala Lys Ala Lys Glu Leu Asp Val Asp Leu Ser
        50                  55                  60

Gly Ile Glu Ile Ile Asp Pro Glu Lys Ser Glu Asn Leu Asn Lys Tyr
65                  70                  75                  80

Ile Thr Ala Phe Tyr Glu Leu Arg Lys Ser Lys Gly Val Thr Met Glu
                    85                  90                  95

Lys Ala Asp Lys Ile Val Arg Asp Pro Leu Tyr Phe Ala Thr Met Met
                100                 105                 110

Val Lys Leu Asp Asp Ala Asp Gly Met Val Ser Gly Ala Val His Thr
            115                 120                 125

Thr Gly Asp Leu Leu Arg Pro Gly Leu Gln Ile Ile Lys Thr Ala Pro
```

```
                    130                 135                 140
Gly Val Ser Val Val Ser Phe Phe Ile Met Gln Val Pro Gly Ser
145                 150                 155                 160

Thr Tyr Gly Glu Gln Gly Thr Leu Ile Phe Ser Asp Cys Ala Val Asn
                165                 170                 175

Pro Asn Pro Asn Glu Asp Gln Leu Ala Ala Ile Ala Ile Ala Thr Ala
                180                 185                 190

Glu Thr Ala Lys Arg Leu Cys Asn Met Asp Pro Lys Val Ala Met Leu
                195                 200                 205

Ser Phe Ser Thr Met Gly Ser Ala Asp Asn Glu Leu Val Asp Lys Val
210                 215                 220

Arg Asn Ala Thr Gln Lys Ala Lys Glu Met Arg Pro Asp Leu Asp Ile
225                 230                 235                 240

Asp Gly Glu Leu Gln Leu Asp Ala Ala Ile Val Lys Lys Val Ala Asp
                245                 250                 255

Gln Lys Ala Pro Asn Ser Lys Val Ala Gly Lys Ala Asn Val Leu Val
                260                 265                 270

Phe Pro Asp Leu Gln Ala Gly Asn Ile Gly Tyr Lys Leu Val Gln Arg
                275                 280                 285

Phe Ala Asn Ala Glu Ala Ile Gly Pro Ile Cys Gln Gly Phe Asp Lys
                290                 295                 300

Pro Ile Asn Asp Leu Ser Arg Gly Cys Ser Ser Asp Asp Ile Val Asn
305                 310                 315                 320

Val Val Ala Leu Thr Ala Val Gln Ala Gln Asn Asn Lys
                325                 330

<210> SEQ ID NO 4
<211> LENGTH: 10558
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (174)..(179)
<223> OTHER INFORMATION: KpnI site
<220> FEATURE:
<221> NAME/KEY: misc_feature
<222> LOCATION: (250)..(879)
<223> OTHER INFORMATION: PmCDA1 (reverse strand)
<220> FEATURE:
<221> NAME/KEY: misc_feature
<222> LOCATION: (1243)..(5346)
<223> OTHER INFORMATION: dCas9 (reverse strand)
<220> FEATURE:
<221> NAME/KEY: misc_feature
<222> LOCATION: (5560)..(5579)
<223> OTHER INFORMATION: Targeting sequence insertion site
<220> FEATURE:
<221> NAME/KEY: misc_feature
<222> LOCATION: (5560)..(5579)
<223> OTHER INFORMATION: "n" can be any of a, t, g or c
<220> FEATURE:
<221> NAME/KEY: misc_feature
<222> LOCATION: (6083)..(6088)
<223> OTHER INFORMATION: BamHI site

<400> SEQUENCE: 4
atcgccattc gccattcagg ctgcgcaact gttgggaagg gcgatcggtg cgggcctctt      60
cgctattacg ccagctggcg aaagggggat gtgctgcaag gcgattaagt tgggtaacgc     120
cagggttttc ccagtcacga cgttgtaaaa cgacggccag tgaattcgag ctcggtaccc     180
ggccgcaaac aacagataaa acgaaaggcc cagtctttcg actgagcctt tcgttttatt     240
```

```
tgatgcctgt caagtaacag caggactctt agtggtgtgg agtatttta cctgaatcat      300 aatggacaac tcgctccgtc gttttcagc tcgcttcaaa gtcttctcaa gccatctatt      360
ctcattcaat tgattgtgcg acgattggat gaatattttc ctgcaacatt ggtagtgttc      420
acttaccatt acattcaacc caccccgtt atctctgagg ttccacagcc caatttgatt      480
cctcgcattt ttctcgtaat agagtttgca agcccagatt tcaaagtgt ggccgttccc      540 ccgcagctcc tggttatacc attctaagat cttttcagcg caatctgcac aaggactcca      600
ggatgagtac caatttatcg tgaattgtcc ggggttgtcg cgcaggtatt cttcgacttt      660
tctaatgcta aagatttcgg cgtgaatgcc acgttctgtc ccgctctgtg gtttattcac      720
agcatagccc caaaaacacg ctctacgttc accccgtcgt tttaattcaa agagaacgta      780
gcatctatgc gacacggatt ttttgttgtt gaaaaactgt tcttaaacg tgtagatgtc      840 caacttctca tggattctca cgtactcagc gtcggtcatc ctagacttat cgtcatcgtc      900
tttgtaatca atatcatgat ccttgtagtc tccgtcgtgg tccttatagt ctccggactc      960
gagcctagac ttatcgtcat cgtctttgta atcaatatca tgatccttgt agtctccgtc     1020
gtggtcctta tagtctccgg aatacttctc cacgtaaggg acaggaatca tcccctctt      1080 tccttcgctg tcctctgcat tccaccactg ctcctcaggc ttatcccgga ttctcaggat     1140
gtctcctttc ttaaagggaa gatcctcttc atcattccca ttaaagtcaa agagggctcg     1200
cacatactca gcagaacctc cacctccaga acctcctcca ccgtcacctc ctagctgact     1260
caaatcaatg cgtgtttcat aaagaccagt gatggattga tggataagag tggcatctaa     1320
aacttctttt gtagacgtat atcgtttacg atcaattgtt gtatcaaaat atttaaaagc     1380
agcgggagct ccaagattcg tcaacgtaaa taaatgaata atattttctg cttgttcacg     1440
tattggtttg tctctatgtt tgttatatgc actaagaact ttatctaaat tggcatctgc     1500
taaaataaca cgcttagaaa attcactgat ttgctcaata atctcatcta aataatgctt     1560
atgctgctcc acaaacaatt gtttttgttc gttatcttct ggactaccct tcaacttttc     1620
ataatgacta gctaaatata aaaaattcac atatttgctt ggcagagcca gctcatttcc     1680 ttttgtaat tctccggcac tagccagcat ccgtttacga ccgttttcta actcaaaaag      1740
actatattta ggtagtttaa tgattaagtc tttttaact tccttatatc ctttagcttc      1800
taaaaagtca atcggatttt tttcaaagga acttctttcc ataattgtga tcccctagtaa    1860 ctctttaacg gatttaact tcttcgattt ccctttttcc accttagcaa ccactaggac      1920
tgaataagct accgttggac tatcaaaacc accatatttt tttggatccc agtcttttt     1980 acgagcaata agcttgtccg aattcttttt tggtaaaatt gactccttgg agaatccgcc     2040
tgtctgtact tctgttttct tgacaatatt gacttggggc atggacaata ctttgcgcac     2100
tgtggcaaaa tctcgcccct tatcccagac aatttctcca gtttccccat tagtttcgat     2160
tagagggcgt ttgcgaatct ctccatttgc aagtgtaatt tctgttttga agaagttcat     2220
gatattagag taaagaaat attttgcggt tgctttgcct atttcttgct cagacttagc     2280 aatcattttta cgaacatcat aaactttata atcaccatag acaaactccg attcaagttt      2340
tggatatttc ttaatcaaag cagttccaac gacggcattt agatacgcat catgggcatg      2400
atggtaattg ttaatctcac gtactttata gaattggaaa tcttttcgga agtcagaaac      2460
taatttagat tttaaggtaa tcactttaac ctctcgaata agtttatcat tttcatcgta      2520
tttagtattc atgcgactat ccaaaatttg tgccacatgc ttagtgattt ggcgagtttc      2580
```

```
aaccaattgg cgtttgataa aaccagcttt atcaagttca ctcaaacctc cacgttcagc    2640
tttcgttaaa ttatcaaact tacgttgagt gattaacttg gcgtttagaa gttgtctcca    2700
atagtttttc atcttttga ctacttcttc acttggaacg ttatccgatt taccacgatt     2760
tttatcagaa cgcgttaaga ccttattgtc tattgaatcg tctttaagga aactttgtgg    2820
aacaatggca tcgacatcat aatcacttaa acgattaata tctaattctt ggtccacata    2880
catgtctctt ccattttgga gataatagag atagagcttt tcattttgca attgagtatt    2940
ttcaacagga tgctctttaa gaatctgact tcctaattct ttgatacctt cttcgattcg    3000
tttcatacgc tctcgcgaat tttctggcc cttttgagtt gtctgatttt cacgtgccat     3060
ttcaataacg atattttctg gcttatgccg ccccattact ttgaccaatt catcaacaac    3120
ttttacagtc tgtaaaatac ctttttaat agcagggcta ccagctaaat ttgcaatatg     3180
ttcatgtaaa ctatcgcctt gtccagacac ttgtgctttt tgaatgtctt ctttaaatgt    3240
caaactatca tcatggatca gctgcataaa attgcgattg gcaaaaccat ctgatttcaa    3300
aaaatctaat attgttttgc cagattgctt atccctaata ccattaatca attttcgaga    3360
caaacgtccc caaccagtat aacggcgacg tttaagctgt ttcatcaccct tatcatcaaa   3420 gaggtgagca tatgttttaa gtcttttcctc aatcatctcc ctatcttcaa ataaggtcaa   3480
tgttaaaaca atatcctcta agatatcttc attttcttca ttatccaaaa aatctttatc    3540
tttaataatt tttagcaaat catggtaggt acctaatgaa gcattaaatc tatcttcaac    3600
tcctgaaatt tcaacactat caaaacattc tatttttttg aaataatctt cttttaattg    3660
cttaacggtt acttttcgat ttgttttgaa gagtaaatca acaatggctt tcttctgttc    3720
acctgaaaga aatgctggtt ttcgcattcc ttcagtaaca tatttgaccct ttgtcaattc   3780 gttataaacc gtaaaatact cataaagcaa actatgtttt ggtagtactt tttcatttgg    3840 aagatttta tcaaagtttg tcatgcgttc aataaatgat tgagctgaag cacctttatc     3900
gacaacttct tcaaaattcc atggggtaat tgtttcttca gacttccgag tcatccatgc    3960
aaaacgacta ttgccacgcg ccaatggacc aacataataa ggaattcgaa aagtcaagat    4020 ttttcaatc ttctcacgat tgtcttttaa aaatggataa aagtcttctt gtcttctcaa     4080
aatagcatgc agctcaccca gtgaatttg atggggaata gagccgttgt caaaggtccg     4140
ttgcttgcgc agcaaatctt cacgatttag tttcaccaat aattcctcag taccatccat    4200
tttttctaaa attggtttga taaatttata aaattcttct tggctagctc ccccatcaat    4260
ataacctgca tatccgtttt ttgattgatc aaaaaagatt tctttatact tttctggaag   4320
ttgttgtcga actaaagctt ttaaaagagt caagtcttga tgatgttcat cgtagcgttt    4380
aatcattgaa gctgataggg gagccttagt tatttcagta tttactctta ggatatctga    4440
aagtaaaata gcatctgata aattcttagc tgccaaaaac aaatcagcat attgatctcc    4500
aatttgcgcc aataaattat ctaaatcatc atcgtaagta tcttttgaaa gctgtaattt    4560
agcatcttct gccaaatcaa aatttgatt aaaattaggg gtcaaaccca atgacaaagc     4620
aatgagattc ccaaataagc cattttctt ctcaccgggg agctgagcaa tgagatttc      4680 taatcgtctt gatttactca atcgtgcaga aagaatcgct ttagcatcta ctccacttgc    4740 gttaatagg ttttcttcaa ataattgatt gtaggtttgt accaactgga taaatagttt    4800
gtccacatca ctattatcag gatttaaatc tccctcaatc aaaaaatgac cacgaaactt    4860
aatcatatgc gctaaggcca aatagattaa gcgcaaatcc gctttatcag tagaatctac    4920 caatttttt cgcagatgat agatagttgg atatttctca tgataagcaa cttcatctac     4980
```

```
tatatttcca aaaataggat gacgttcatg cttcttgtct tcttccacca aaaaagactc    5040
ttcaagtcga tgaaagaaac tatcatctac tttcgccatc tcatttgaaa aaatctcctg    5100
tagataacaa atacgattct tccgacgtgt ataccttcta cgagctgtcc gtttgagacg    5160
agtcgcttcc gctgtctctc cactgtcaaa taaaagagcc cctataagat tttttttgat    5220
actgtggcgg tctgtatttc ccagaaccTt gaacttttta gacggaacct tatattcatc    5280
agtgatcacc gcccatccga cgctatttgt gccgatagct aagcctattg agtatttctt    5340
atccattttt gcctcctaaa atgggccctt taaattaaat ccataatgag tttgatgatt    5400
tcaataatag ttttaatgac ctccgaaatt agtttaatat gctttaattt ttctttttca    5460
aaatatctct tcaaaaaata ttacccaata cttaataata aatagattat aacacaaaat    5520
tcttttgaca agtagtttat tttgttataa ttctatagtn nnnnnnnnnn nnnnnnnnng    5580
ttttagagct agaaatagca agttaaaata aggctagtcc gttatcaact tgaaaaagtg    5640
gcaccgagtc ggtgcttttt ttgatacttc tattctactc tgactgcaaa ccaaaaaaac    5700
aagcgctttc aaaacgcttg ttttatcatt tttagggaaa ttaatctctt aatccttTTa    5760
tcattctaca tttaggcgct gccatcttgc taaacctact aagctccaca ggatgatttc    5820
gtaatcccgc aagaggcccg gcagtaccgg cataaccaag cctatgccta cagcatccag    5880
ggtgacggtg ccgaggatga cgatgagcgc attgttagat tcatacacg gtgcctgact    5940 gcgttagcaa tttaactgtg ataaactacc gcattaaagc ttatcgatga taagctgtca    6000
aacatgagaa ttcaacttta tatcgtatgg ggctgacttc aggtgctaca tttgaagaga    6060
taaattgcac tgaaatctag tcggatcctc gctcactgac tcgctgcgct cggtcgttcg    6120
gctgcggcga gcggtatcag ctcactcaaa ggcggtaata cggttatcca cagaatcagg    6180
ggataacgca ggaaagaaca tgtgagcaaa aggccagcaa aaggccagga accgtaaaaa    6240
ggccgcgttg ctggcgtttt tccataggct ccgcccccct gacgagcatc acaaaaatcg    6300
acgctcaagt cagaggtggc gaaacccgac aggactataa agataccagg cgtttccccc    6360
tggaagctcc ctcgtgcgct ctcctgttcc gaccctgccg cttaccggat acctgtccgc    6420
ctttctccct tcgggaagcg tggcgctttc tcatagctca cgctgtaggt atctcagttc    6480
ggtgtaggtc gttcgctcca agctgggctg tgtgcacgaa ccccccgttc agcccgaccg    6540
ctgcgcctta tccggtaact atcgtcttga gtccaacccg gtaagacacg acttatcgcc    6600
actggcagca gccactggta acaggattag cagagcgagg tatgtaggcg gtgctacaga    6660
gttcttgaag tggtggccta actacggcta cactagaagg acagtatttg gtatctgcgc    6720
tctgctgaag ccagttacct tcggaaaaag agttggtagc tcttgatccg gcaaacaaac    6780
caccgctggt agcggtggtt ttttttgttTg caagcagcag attacgcgca gaaaaaaagg    6840
atctcaagaa gatcctttga tcttttctac ggggtctgac gctcagtgga acgaaaactc    6900
acgttaaggg attttggtca tgagattatc aaaaaggatc ttcacctaga tccttttaaa    6960
ttaaaaatga agttttaaat caatctaaag tatatatgag taaacttggt ctgacagtta    7020
ccaatgctta atcagtgagg cacctatctc agcgatctgt ctatttcgtt catccatagt    7080
tgcctgactc cccgtcgtgt agataactac gatacgggag gcttaccat ctggccccag    7140 tgctgcaatg ataccgcgag aaccacgctc accggctcca gatttatcag caataaacca    7200
gccagccgga agggccgagc gcagaagtgg tcctgcaact ttatccgcct ccatccagtc    7260
tattaattgt tgccgggaag ctagagtaag tagttcgcca gttaatagtt tgcgcaacgt    7320
```

```
tgttgccatt gctgcaggca tcgtggtgtc acgctcgtcg tttggtatgg cttcattcag      7380
ctccggttcc caacgatcaa ggcgagttac atgatccccc atgttgtgca aaaaagcggt      7440
tagctccttc ggtcctccga tcgttgtcag aagtaagttg gccgcagtgt tatcactcat      7500
ggttatggca gcactgcata attctcttac tgtcatgcca tccgtaagat gcttttctgt      7560
gactggtgag tactcaacca agtcattctg agaatagtgt atgcggcgac cgagttgctc      7620
ttgcccggcg tcaacacggg ataataccgc gccacatagc agaactttaa aagtgctcat      7680
cattggaaaa cgttcttcgg ggcgaaaact ctcaaggatc ttaccgctgt tgagatccag      7740
ttcgatgtaa cccactcgtg cacccaactg atcttcagca tcttttactt tcaccagcgt      7800
ttctgggtga gcaaaaacag gaaggcaaaa tgccgcaaaa aagggaataa gggcgacacg      7860
gaaatgttga atactcatac tcttcctttt tcaatattat tgaagcattt atcagggtta      7920
ttgtctcatg agcggataca tatttgaatg tatttagaaa aataaacaaa tagggggttcc      7980 gcgcacattt ccccgaaaag tgccacctga cgtctaagaa accattatta tcatgacatt      8040
aacctataaa aataggcgta tcacgaggcc ctttcgtctc gcgcgtttcg gtgatgacgg      8100
tgaaaacctc tgacacatgc agctcccgga cggtcaca gcttgtctgt aagcggatgc      8160
cgggagcaga caagcccgtc agggcgcgtc agcgggtgtt ggcgggtgtc ggggctggct      8220
taactatgcg gcatcagagc agattgtact gagagtgcac catatgcggt gtgaaatacc      8280
gcacagatgc gtaaggagaa ataccgcat caggcgatta tgtcttttgc gcattcactt      8340
cttttctata taaatatgag cgaagcgaat aagcgtcgga aaagcagcaa aaagtttcct      8400
ttttgctgtt ggagcatggg ggttcagggg gtgcagtatc tgacgtcaat gccgagcgaa      8460
agcgagccga agggtagcat ttacgttaga taaccccctg atatgctccg acgctttata      8520 tagaaagaa gattcaacta ggtaaaatct taatataggt tgagatgata aggtttataa      8580
ggaatttgtt tgttctaatt tttcactcat tttgttctaa tttctttttaa caaatgttct      8640 ttttttttta gaacagttat gatatagtta gaatagttta aaataaggag tgagaaaaag      8700
atgaaagaaa gatatggaac agtctataaa ggctctcaga ggctcataga cgaagaaagt      8760
ggagaagtca tagaggtaga caagttatac cgtaaacaaa cgtctggtaa cttcgtaaag      8820
gcatatatag tgcaattaat aagtatgtta gatatgattg gcggaaaaaa acttaaaatc      8880
gttaactata tcctagataa tgtccactta agtaacaata caatgatagc tacaacaaga      8940
gaaatagcaa aagctacagg aacaagtcta caaacagtaa taacaacact taaaatctta      9000
gaagaaggaa atattataaa aagaaaaact ggagtattaa tgttaaaccc tgaactacta      9060
atgagaggcg acgaccaaaa acaaaaatac ctcttactcg aatttgggaa ctttgagcaa      9120
gaggcaaatg aaatagattg acctcccaat aacaccacgt agttattggg aggtcaatct      9180
atgaaatgcg attaagcttt ttctaattca cataagcgtg caggtttaaa gtacataaaa      9240
aatataatga aaaaagcat cattatacta acgttatacc aacattatac tctcattata      9300
ctaattgctt attccaattt cctattggtt ggaaccaaca ggcgttagtg tgttgttgag      9360
ttggtacttt catgggatta atcccatgaa accccccaacc aactcgccaa agctttggct      9420
aacacacacg ccattccaac caatagtttt tcggcataa agccatgctc tgacgcttaa      9480
atgcactaat gccttaaaaa aacattaaag tctaacacac tagacttatt tacttcgtaa      9540
ttaagtcgtt aaaccgtgtg ctctacgacc aaaagtataa aacctttaag aactttcttt      9600
tttcttgtaa aaaagaaac tagataaatc tctcatatct tttattcaat aatcgcatca      9660
gattgcagta taaatttaac gatcactcat catgttcata tttatcagag ctcgtgctat      9720
```

```
aattatacta attttataag gaggaaaaaa taaagagggt tataatgaac gagaaaaata    9780
taaaacacag tcaaaacttt attacttcaa aacataatat agataaaata atgacaaata    9840
taagattaaa tgaacatgat aatatctttg aaatcggctc aggaaaaggg cattttaccc    9900
ttgaattagt acagaggtgt aatttcgtaa ctgccattga aatagaccat aaattatgca    9960
aaactacaga aaataaactt gttgatcacg ataatttcca agttttaaac aaggatatat   10020
tgcagtttaa atttcctaaa aaccaatcct ataaatatt tggtaatata ccttataaca   10080
taagtacgga tataatacgc aaaattgttt ttgatagtat agctgatgag atttatttaa   10140
tcgtggaata cgggtttgct aaaagattat taaatacaaa acgctcattg gcattatttt   10200
taatggcaga agttgatatt tctatattaa gtatggttcc aagagaatat tttcatccta   10260
aacctaaagt gaatagctca cttatcagat taaatagaaa aaaatcaaga atatcacaca   10320
aagataaaca gaagtataat tatttcgtta tgaaatgggt taacaaagaa tacaagaaaa   10380
tatttacaaa aaatcaattt aacaattcct taaaacatgc aggaattgac gatttaaaca   10440
atattagctt tgaacaattc ttatctcttt tcaatagcta taaattattt aataagtaag   10500
ttaagggatg cataaactgc atcccttaac ttgttttcg tgtacctatt ttttgtga      10558
```

<210> SEQ ID NO 5
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 5

```
ctcttgataa atcatttat                                                  19
```

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 6

```
gctgcccata ttttttcat a                                                21
```

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7

```
gcccttatg aaagggatta tattcag                                          27
```

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8

```
gcttgtacag cagttaatgc aac                                             23
```

<210> SEQ ID NO 9

```
<211> LENGTH: 22
<212> TYPE: DNA
<213> ORGANISM: Artificial Sequence
<220> FEATURE:
<223> OTHER INFORMATION: Primer

<400> SEQUENCE: 9
ggtgttacag gaaatgttgc ag                                             22

<210> SEQ ID NO 10
<211> LENGTH: 20
<212> TYPE: DNA
<213> ORGANISM: Clostridium saccharoperbutylacetonicum

<400> SEQUENCE: 10
ataaatgatt tatcaagagg                                                20

<210> SEQ ID NO 11
<211> LENGTH: 20
<212> TYPE: DNA
<213> ORGANISM: Clostridium saccharoperbutylacetonicum

<400> SEQUENCE: 11
ataaatgatt tatcaaaagg                                                20

<210> SEQ ID NO 12
<211> LENGTH: 20
<212> TYPE: DNA
<213> ORGANISM: Clostridium saccharoperbutylacetonicum

<400> SEQUENCE: 12
ataaatgatt tatcaagaag                                                20

<210> SEQ ID NO 13
<211> LENGTH: 20
<212> TYPE: DNA
<213> ORGANISM: Clostridium saccharoperbutylacetonicum

<400> SEQUENCE: 13
ataaatgatt tatcaaaaaa                                                20

<210> SEQ ID NO 14
<211> LENGTH: 25
<212> TYPE: DNA
<213> ORGANISM: Clostridium saccharoperbutylacetonicum

<400> SEQUENCE: 14
ccttatgaaa aaaatatggg cagca                                          25

<210> SEQ ID NO 15
<211> LENGTH: 25
<212> TYPE: DNA
<213> ORGANISM: Clostridium saccharoperbutylacetonicum

<400> SEQUENCE: 15
caaaaaaaaa aaaatatgga caaca                                          25

<210> SEQ ID NO 16
<211> LENGTH: 25
<212> TYPE: DNA
<213> ORGANISM: Clostridium saccharoperbutylacetonicum

<400> SEQUENCE: 16
ccttatgaaa aaaatatgaa cagca                                          25
```

<210> SEQ ID NO 17
<211> LENGTH: 25
<212> TYPE: DNA
<213> ORGANISM: Clostridium saccharoperbutylacetonicum

<400> SEQUENCE: 17
ccttatgaaa aaaatatgga cagca                                         25

<210> SEQ ID NO 18
<211> LENGTH: 9299
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(6)
<223> OTHER INFORMATION: HindIII site
<220> FEATURE:
<221> NAME/KEY: misc_feature
<222> LOCATION: (3370)..(3375)
<223> OTHER INFORMATION: XhoI site
<220> FEATURE:
<221> NAME/KEY: misc_feature
<222> LOCATION: (3463)..(4092)
<223> OTHER INFORMATION: PmCDA1 (reverse strand)
<220> FEATURE:
<221> NAME/KEY: misc_feature
<222> LOCATION: (4456)..(8559)
<223> OTHER INFORMATION: dCas9 (reverse strand)
<220> FEATURE:
<221> NAME/KEY: misc_feature
<222> LOCATION: (8773)..(8792)
<223> OTHER INFORMATION: Targeting sequence insertion site
<220> FEATURE:
<221> NAME/KEY: misc_feature
<222> LOCATION: (8773)..(8792)
<223> OTHER INFORMATION: "n" can be any of a, t, g or c

<400> SEQUENCE: 18
aagcttaaca ggatgctagg ggggagccgc cgctccgtcg cccccctgcgg ggggcttccg      60 tatgcggcag gcatcccctc gcatgcaggt agggaacaat tacattgtct ttgattgtaa     120
aaatgctgtt gacaggacac taaatggtgt cgtattctca aagtaacacc atttggtgtc     180
caattgcaag tcatttggta accttaattg gatcagacaa ggtaaaggat aaaacagcac     240
aattccaaga aaaacacgat ttagaaccta aaagaacga atttgaacta actcataacc     300
gagaggtaaa aaaagaacga agtcgagatc agggaatgag tttataaaat aaaaaaagca     360
cctgaaaagg tgtctttttt tgatggtttt gaacttgttc tttcttatct tgatacatat     420
agaaataacg tcattttttat tttagttgct gaaaggtgcg ttgaagtgtt ggtatgtatg     480
tgttttaaag tattgaaaac ccttaaaatt ggttgcacag aaaaacccca tctgttaaag     540
ttataagtga ctaaacaaat aactaaatag atgggggttt cttttaatat tatgtgtcct     600
aatagtagca tttattcaga tgaaaaatca agggttttag tggacaagac aaaaagtgga     660
aaagtgaggc cttggagaga aagaaaatc gctaatgttg attactttga acttctgcat     720
attcttgaat ttaaaaaggc tgaaagagta aaagattgtg ctgaaatatt agagtataaa     780
caaaatcgtg aaacaggcga agaaagttg tatcgagtgt ggttttgtaa atccaggctt     840
tgtccaatgt gcaactggag gagagcaatg aaacatggca ttcagtcaca aaaggttgtt     900
gctgaagtta ttaaacaaaa gccaacagtt cgttggttgt ttctcacatt aacagttaaa     960
aatgtttatg atggcgaaga attaaataag agtttgtcag atatggctca aggatttcgc    1020

-continued

```
cgaatgatgc aatataaaaa aattaataaa aatcttgttg gttttatgcg tgcaacggaa    1080
gtgacaataa ataataaaga taattcttat aatcagcaca tgcatgtatt ggtatgtgtg    1140
gaaccaactt attttaagaa tacagaaaac tacgtgaatc aaaaacaatg gattcaattt    1200
tggaaaaagg caatgaaatt agactatgat ccaaatgtaa aagttcaaat gattcgaccg    1260
aaaaataaat ataaatcgga tatacaatcg gcaattgacg aaactgcaaa atatcctgta    1320
aaggatacgg attttatgac cgatgatgaa gaaaagaatt tgaaacgttt gtctgatttg    1380
gaggaaggtt tacaccgtaa aaggttaatc tcctatggtg gtttgttaaa agaaatacat    1440
aaaaaattaa accttgatga cacagaagaa ggcgatttga ttcatacaga tgatgacgaa    1500
aaagccgatg aagatggatt ttctattatt gcaatgtgga attgggaacg gaaaaattat    1560
tttattaaag agtagttcaa caaacgggcc agtttgttga agattagatg ctataattgt    1620
tattaaaagg attgaaggat gcttaggaag acgagttatt aatagctgaa taagaacggt    1680
gctctccaaa tattcttatt tagaaaagca aatctaaaat tatctgaaaa gggaatgaga    1740
atagtgaatg gaccaataat aatgactaga gaagaaagaa tgaagattgt ccatgaaatt    1800
aaggaacgaa tattggataa atatggggat gatgttaagg ctattggtgt ttatggctct    1860
cttggtcgtc agactgatgg gccctattcg gatattgaga tgatgtgtgt catgtcaaca    1920
gaggaagcag agttcagcca tgaatggaca accggtgagt ggaaggtgga agtgaatttt    1980
gatagcgaag agattctact agattatgca tctcaggtgg aatcagattg gccgcttaca    2040
catggtcaat ttttctctat tttgccgatt tatgattcag gtggatactt agagaaagtg    2100
tatcaaactg ctaaatcggt agaagcccaa acgttccacg atgcgatttg tgcccttatc    2160
gtagaagagc tgtttgaata tgcaggcaaa tggcgtaata ttcgtgtgca aggaccgaca    2220
acatttctac catccttgac tgtacaggta gcaatggcag gtgccatgtt gattggtctg    2280
catcatcgca tctgttatac gacgagcgct tcggtcttaa ctgaagcagt taagcaatca    2340
gatcttcctt caggttatga ccatctgtgc cagttcgtaa tgtctggtca actttccgac    2400
tctgagaaac ttctggaatc gctagagaat ttctggaatg ggattcagga gtggacagaa    2460
cgacacggat atatagtgga tgtgtcaaaa cgcataccat tttgaacgat gacctctaat    2520
aattgttaat catgttggtt acgtatttat taacttctcc tagtattagt aattatcatg    2580
gctgtcatgg cgcattaacg gaataaaggg tgtgcttaaa tcgggccggc tgaataaaag    2640
atacgagaga cctctcttgt atctttttta ttttgagtgg ttttgtccgt tacactagaa    2700
aaccgaaaga caataaaaat tttattcttg ctgagtctgg ctttcggtaa gctagacaaa    2760
acggacaaaa taaaaattgg caagggttta aaggtggaga ttttttgagt gatcttctca    2820
aaaaatacta cctgtccctt gctgattttt aaacgagcac gagagcaaaa ccccccttfg    2880 ctgaggtggc agagggcagg ttttttttgtt tctttttct cgtaaaaaaa agaaaggtct    2940
taaaggtttt atggttttgg tcggcactgc cgacagcctc gcagagcaca cactttcata    3000
tggcggccgc gaacaattat cttcaacatg gactaatctt gtccttgaat caagtactgt    3060
gatccgccca cgtaccttct cagcttctcc ccaaactgtt agaactcgaa cgtccttatc    3120
ttcttttgct tccaccagtt gattgccaag ttcctctagt tcaaactcat cccgagttgg    3180
ccgtttaggt atatttgact ttgccaatgc cgcccctcct tattgaattg agtatcagtc    3240
ttacaccgat ataaaaatcc atgaaaacat tttacttaca aatagattaa ggaaaatttt    3300
tctaatataa atgtttgaaa taatttacct aatttagtat aatttgcttt gttgcaaaaa    3360
tataccaaac tcgagaattc gagctcggta cccggccgca aacaacagat aaaacgaaag    3420
```

```
gcccagtctt tcgactgagc ctttcgtttt atttgatgcc tgtcaagtaa cagcaggact    3480
cttagtggtg tggagtattt ttacctgaat cataatggac aactcgctcc gtcgttttc     3540
agctcgcttc aaagtcttct caagccatct attctcattc aattgattgt gcgacgattg    3600
gatgaatatt ttcctgcaac attggtagtg ttcacttacc attacattca acccaacccc    3660
gttatctctg aggttccaca gcccaatttg attcctcgca ttttctcgt aatagagttt     3720
gcaagcccag attttcaaag tgtggccgtt cccccgcagc tcctggttat accattctaa    3780
gatcttttca gcgcaatctg cacaaggact ccaggatgag taccaattta tcgtgaattg    3840
tccggggttg tcgcgcaggt attcttcgac ttttctaatg ctaaagattt cggcgtgaat    3900
gccacgttct gtcccgctct gtggtttatt cacagcatag ccccaaaaac acgctctacg    3960
ttcaccccgt cgttttaatt caaagagaac gtagcatcta tgcgacacgg attttttgtt    4020
gttgaaaaac tgtttcttaa acgtgtagat gtccaacttc tcatggattc tcacgtactc    4080
agcgtcggtc atcctagact tatcgtcatc gtctttgtaa tcaatatcat gatccttgta    4140
gtctccgtcg tggtccttat agtctccgga ctcgagccta gacttatcgt catcgtcttt    4200
gtaatcaata tcatgatcct tgtagtctcc gtcgtggtcc ttatagtctc cggaatactt    4260
ctccacgtaa gggacaggaa tcatcccct ctttccttcg ctgtcctctg cattccacca     4320
ctgctcctca ggcttatccc ggattctcag gatgtctcct tcttaaagg gaagatcctc     4380
ttcatcattc ccattaaagt caaagagggc tcgcacatac tcagcagaac ctccacctcc    4440
agaacctcct ccaccgtcac ctcctagctg actcaaatca atgcgtgttt cataaagacc    4500
agtgatggat tgatggataa gagtggcatc taaaacttct tttgtagacg tatatcgttt    4560
acgatcaatt gttgtatcaa atatttaaa agcagcggga gctccaagat tcgtcaacgt     4620
aaataaatga ataatatttt ctgcttgttc acgtattggt ttgtctctat gtttgttata    4680
tgcactaaga actttatcta aattggcatc tgctaaaata acacgcttag aaaattcact    4740
gatttgctca ataatctcat ctaaataatg cttatgctgc tccacaaaca attgtttttg    4800
ttcgttatct tctggactac ccttcaactt ttcataatga ctagctaaat ataaaaaatt    4860
cacatatttg cttggcagag ccagctcatt tcctttttgt aattctccgg cactagccag    4920
catccgttta cgaccgtttt ctaactcaaa aagactatat ttaggtagtt taatgattaa    4980
gtcttttta acttccttat atcctttagc ttctaaaaag tcaatcggat tttttcaaa     5040
ggaacttctt tccataattg tgatccctag taactctta acggatttta acttcttcga    5100
tttccctttt tccaccttag caaccactag gactgaataa gctaccgttg gactatcaaa    5160
accaccatat ttttttggat cccagtcttt tttacgagca ataagcttgt ccgaatttct    5220
ttttggtaaa attgactcct tggagaatcc gcctgtctgt acttctgttt tcttgacaat    5280
attgacttgg ggcatggaca atactttgcg cactgtggca aaatctcgcc ctttatccca    5340
gacaatttct ccagttttccc cattagtttc gattagaggg cgtttgcgaa tctctccatt    5400
tgcaagtgta atttctgttt tgaagaagtt catgatatta gagtaaaaga aatattttgc    5460
ggttgctttg cctatttctt gctcagactt agcaatcatt ttacgaacat cataaacttt    5520
ataatcacca tagacaaact ccgattcaag ttttggatat ttcttaatca aagcagttcc    5580
aacgacggca tttagatacg catcatgggc atgatggtaa ttgttaatct cacgtacttt    5640
atagaattgg aaatctttc ggaagtcaga aactaattta gatttaagg taatcacttt      5700
aacctctcga ataagtttat cattttcatc gtatttagta ttcatgcgac tatccaaaat    5760
```

```
ttgtgccaca tgcttagtga tttggcgagt ttcaaccaat tggcgtttga taaaaccagc  5820
tttatcaagt tcactcaaac ctccacgttc agctttcgtt aaattatcaa acttacgttg  5880
agtgattaac ttggcgttta aagttgtctc caatagtttt tcatctttt tgactacttc  5940
ttcacttgga acgttatccg atttaccacg atttttatca aacgcgtta agaccttatt  6000
gtctattgaa tcgtctttaa ggaaactttg tggaacaatg gcatcgacat cataatcact  6060
taaacgatta atatctaatt cttggtccac atacatgtct cttccatttt ggagataata  6120
gagatagagc ttttcatttt gcaattgagt attttcaaca ggatgctctt taagaatctg  6180
acttcctaat tctttgatac cttcttcgat tcgtttcata cgctctcgcg aattttttctg  6240
gccctttttga gttgtctgat tttcacgtgc catttcaata acgatatttt ctggcttatg  6300
ccgccccatt actttgacca attcatcaac aactttaca gtctgtaaaa taccttttt  6360
aatagcaggg ctaccagcta aatttgcaat atgttcatgt aaactatcgc cttgtccaga  6420
cacttgtgct ttttgaatgt cttctttaaa tgtcaaacta tcatcatgga tcagctgcat  6480
aaaattgcga ttggcaaaac catctgattt caaaaaatct aatattgttt tgccagattg  6540
cttatcccta ataccattaa tcaattttcg agacaaacgt ccccaaccag tataacggcg  6600
acgtttaagc tgtttcatca ccttatcatc aaagaggtga gcatatgttt taagtctttc  6660
ctcaatcatc tccctatctt caaataaggt caatgttaaa acaatatcct ctaagatatc  6720
ttcatttttct tcattatcca aaaaatcttt atctttaata attttttagca aatcatggta  6780
ggtacctaat gaagcattaa atctatcttc aactcctgaa atttcaacac tatcaaaaca  6840
ttctattttt ttgaaataat cttcttttaa ttgcttaacg gttacttttc gatttgtttt  6900
gaagagtaaa tcaacaatgg ctttcttctg ttcacctgaa agaaatgctg gttttcgcat  6960
tccttcagta acatatttga cctttgtcaa ttcgttataa accgtaaaat actcataaag  7020
caaactatgt tttggtagta cttttttcatt tggaagattt ttatcaaagt ttgtcatgcg  7080
ttcaataaat gattgagctg aagcaccttt atcgacaact tcttcaaaat tccatggggt  7140
aattgtttct tcagacttcc gagtcatcca tgcaaaacga ctattgccac gcgccaatgg  7200
accaacataa taaggaattc gaaaagtcaa gattttttca atcttctcac gattgtcttt  7260
taaaaatgga taaaagtctt cttgtcttct caaaatagca tgcagctcac ccaagtgaat  7320
ttgatgggga atagagccgt tgtcaaaggt ccgttgcttg cgcagcaaat cttcacgatt  7380
tagtttcacc aataattcct cagtaccatc catttttttct aaaattggtt tgataaattt  7440
ataaaattct tcttggctag ctcccccatc aatataaccct gcatatccgt ttttttgattg  7500
atcaaaaaag atttctttat acttttctgg aagttgttgt cgaactaaag cttttaaaag  7560
agtcaagtct tgatgatgtt catcgtagcg tttaatcatt gaagctgata ggggagcctt  7620
agttatttca gtatttactc ttaggatatc tgaaagtaaa atagcatctg ataaattctt  7680
agctgccaaa aacaaatcag catattgatc tccaatttgc gccaataaat tatctaaatc  7740
atcatcgtaa gtatctttttg aaagctgtaa tttagcatct tctgccaaat caaaatttga  7800
tttaaaatta ggggtcaaac ccaatgacaa agcaatgaga ttcccaaata agccatttttt  7860
cttctcaccg gggagctgag caatgagatt ttctaatcgt cttgatttac tcaatcgtgc  7920
agaaagaatc gctttagcat ctactccact tgcgttaata gggttttctt caaataattg  7980
attgtaggtt tgtaccaact ggataaatag tttgtccaca tcactattat caggatttaa  8040
atctccctca atcaaaaaat gaccacgaaa cttaatcata tgcgctaagg ccaaaatagat  8100
taagcgcaaa tccgctttat cagtagaatc taccaatttt tttcgcagat gatagatagt  8160
```

-continued

```
tggatatttc tcatgataag caacttcatc tactatattt ccaaaaatag gatgacgttc    8220
atgcttcttg tcttcttcca ccaaaaaaga ctcttcaagt cgatgaaaga aactatcatc    8280
tactttcgcc atctcatttg aaaaaatctc ctgtagataa caaatacgat tcttccgacg    8340
tgtataccct ctacgagctg tccgtttgag acgagtcgct tccgctgtct ctccactgtc    8400
aaataaaaga gccctataa gattttttt gatactgtgg cggtctgtat ttcccagaac      8460
cttgaacttt ttagacggaa ccttatattc atcagtgatc accgcccatc cgacgctatt    8520
tgtgccgata gctaagccta ttgagtattt cttatccatt tttgcctcct aaaatgggcc    8580 cttttaaatta aatccataat gagtttgatg atttcaataa tagtttaat gacctccgaa    8640 attagtttaa tatgctttaa ttttctttt tcaaaatatc tcttcaaaaa atattaccca    8700
atacttaata ataaatagat tataacacaa aattctttg acaagtagtt tattttgtta    8760
taattctata gtnnnnnnnn nnnnnnnnn nngttttaga gctagaaata gcaagttaaa    8820
ataaggctag tccgttatca acttgaaaaa gtggcaccga tcggtgcttt ttttgatac     8880 ttctattcta ctctgactgc aaaccaaaaa acaagcgct ttcaaaacgc ttgttttatc     8940 attttaggg aaattaatct cttaatcctt ttatcattct acatttaggc gctgccatct    9000
tgctaaacct actaagctcc acaggatgat ttcgtaatcc cgcaagaggc ccggcagtac    9060
cggcataacc aagcctatgc ctacagcatc cagggtgacg gtgccgagga tgacgatgag    9120
cgcattgtta gatttcatac acggtgcctg actgcgttag caatttaact gtgataaact    9180
accgcattaa agcttatcga tgataagctg tcaaacatga gaattacaac ttatatcgta    9240
tggggctgac ttcaggtgct acatttgaag agataaattg cactgaaatc tagtcggat    9299
```

<210> SEQ ID NO 19
<211> LENGTH: 2466
<212> TYPE: DNA
<213> ORGANISM: Corynebacterium glutamicum
<220> FEATURE:
<221> NAME/KEY: CDS
<222> LOCATION: (1)..(2466)

<400> SEQUENCE: 19

```
atg aag gat aat gaa gat ttc gat cca gat tca cca gca acc gaa gct        48
Met Lys Asp Asn Glu Asp Phe Asp Pro Asp Ser Pro Ala Thr Glu Ala
1               5                   10                  15 gtt gcc ttc aac cct ttc gac gat gac gat gag gat gat tcc ccc gct        96
Val Ala Phe Asn Pro Phe Asp Asp Asp Glu Asp Asp Ser Pro Ala
            20                  25                  30 acc tca gcc gtt gcc ttt aac cct ttt gaa gat gac gat gac gac gat       144
Thr Ser Ala Val Ala Phe Asn Pro Phe Glu Asp Asp Asp Asp Asp Asp
        35                  40                  45 gag ttc caa ggc gaa ggc cta gaa ttc ctg ctg cgc gac ctc gac aat       192
Glu Phe Gln Gly Glu Gly Leu Glu Phe Leu Leu Arg Asp Leu Asp Asn
    50                  55                  60 ctg cga gcc acc caa ggt caa atg gtg gtg gaa caa cca gca gtt gaa       240
Leu Arg Ala Thr Gln Gly Gln Met Val Val Glu Gln Pro Ala Val Glu
65                  70                  75                  80 gac agc ctc ggg tca gca tct gcg cat acg gag aca act gcg gcc tca       288
Asp Ser Leu Gly Ser Ala Ser Ala His Thr Glu Thr Thr Ala Ala Ser
                85                  90                  95 ctg cgt ccc cgc cca gag gtg gat cca agt gag agg agt cgt cga caa       336
Leu Arg Pro Arg Pro Glu Val Asp Pro Ser Glu Arg Ser Arg Arg Gln
            100                 105                 110 gca att tcg ctg ttc cgc gaa cgg cgc cgc gta agg cgc caa tcc cgc       384
```

|   |   |   |   |   |   |   |   |   |   |   |   |   |   |   |   |     |
|---|---|---|---|---|---|---|---|---|---|---|---|---|---|---|---|-----|
| Ala | Ile | Ser | Leu | Phe | Arg | Glu | Arg | Arg | Val | Arg | Gln | Ser | Arg |   |   |     |
|     |     |     |     |     | 115 |     |     | 120 |     |     |     | 125 |     |   |   |     |
| cca | gtt | gct | gat | ggc | atg | gtg | gaa | ttg | ccg | ttc | atc | acc | ccc | aaa | ccg | 432 |
| Pro | Val | Ala | Asp | Gly | Met | Val | Glu | Leu | Pro | Phe | Ile | Thr | Pro | Lys | Pro |     |
|     | 130 |     |     |     |     | 135 |     |     |     |     | 140 |     |     |     |     |     |
| gaa | gat | gag | ctc | ctc | atc | gac | ccg | gaa | aag | aag | cgc | aaa | cct | ggt | gtg | 480 |
| Glu | Asp | Glu | Leu | Leu | Ile | Asp | Pro | Glu | Lys | Lys | Arg | Lys | Pro | Gly | Val |     |
| 145 |     |     |     |     | 150 |     |     |     |     | 155 |     |     |     |     | 160 |     |
| gca | gcg | ccg | caa | ctt | gtc | gcg | ggc | gat | atc | gtc | gca | gag | caa | tat | gaa | 528 |
| Ala | Ala | Pro | Gln | Leu | Val | Ala | Gly | Asp | Ile | Val | Ala | Glu | Gln | Tyr | Glu |     |
|     |     |     |     | 165 |     |     |     |     | 170 |     |     |     |     | 175 |     |     |
| gtc | ctc | ggc | gtc | atc | gcg | cac | ggc | ggc | atg | ggt | tgg | att | tac | ctc | gcc | 576 |
| Val | Leu | Gly | Val | Ile | Ala | His | Gly | Gly | Met | Gly | Trp | Ile | Tyr | Leu | Ala |     |
|     |     |     | 180 |     |     |     |     | 185 |     |     |     |     | 190 |     |     |     |
| aac | gac | cgc | aat | gtg | tcc | ggc | cgc | atc | gtg | gtg | ctc | aaa | ggc | atg | atg | 624 |
| Asn | Asp | Arg | Asn | Val | Ser | Gly | Arg | Ile | Val | Val | Leu | Lys | Gly | Met | Met |     |
|     |     | 195 |     |     |     |     | 200 |     |     |     |     | 205 |     |     |     |     |
| gcg | caa | tct | tcc | gtt | caa | gac | caa | ggc | acc | gct | gaa | gcc | gaa | cgc | gaa | 672 |
| Ala | Gln | Ser | Ser | Val | Gln | Asp | Gln | Gly | Thr | Ala | Glu | Ala | Glu | Arg | Glu |     |
|     | 210 |     |     |     |     | 215 |     |     |     |     | 220 |     |     |     |     |     |
| ttc | ctc | gcc | gac | atc | acc | cac | ccc | ggc | atc | gtg | aag | gcc | tac | aac | ttc | 720 |
| Phe | Leu | Ala | Asp | Ile | Thr | His | Pro | Gly | Ile | Val | Lys | Ala | Tyr | Asn | Phe |     |
| 225 |     |     |     |     | 230 |     |     |     |     | 235 |     |     |     |     | 240 |     |
| atc | gac | gac | ccc | cgc | gtc | ccc | ggc | gga | ttc | atc | gtc | atg | gaa | tac | gtc | 768 |
| Ile | Asp | Asp | Pro | Arg | Val | Pro | Gly | Gly | Phe | Ile | Val | Met | Glu | Tyr | Val |     |
|     |     |     |     | 245 |     |     |     |     | 250 |     |     |     |     | 255 |     |     |
| aac | ggc | ccc | tcc | ctg | aaa | gac | cgc | tgc | aaa | gcc | caa | ccc | gac | ggc | gtg | 816 |
| Asn | Gly | Pro | Ser | Leu | Lys | Asp | Arg | Cys | Lys | Ala | Gln | Pro | Asp | Gly | Val |     |
|     |     |     | 260 |     |     |     |     | 265 |     |     |     |     | 270 |     |     |     |
| ctc | cgc | gtc | gac | ctc | gcc | atc | ggc | tac | atc | ctc | gaa | ctc | ctc | ccc | gcc | 864 |
| Leu | Arg | Val | Asp | Leu | Ala | Ile | Gly | Tyr | Ile | Leu | Glu | Leu | Leu | Pro | Ala |     |
|     |     | 275 |     |     |     |     | 280 |     |     |     |     | 285 |     |     |     |     |
| atg | gac | tac | ctg | cac | caa | cgc | ggc | gta | gtg | tac | aac | gac | ctc | aaa | ccc | 912 |
| Met | Asp | Tyr | Leu | His | Gln | Arg | Gly | Val | Val | Tyr | Asn | Asp | Leu | Lys | Pro |     |
|     | 290 |     |     |     |     | 295 |     |     |     |     | 300 |     |     |     |     |     |
| gaa | aac | gtc | atc | gcc | acc | gaa | gac | caa | gtt | aaa | ctc | atc | gac | ctc | ggc | 960 |
| Glu | Asn | Val | Ile | Ala | Thr | Glu | Asp | Gln | Val | Lys | Leu | Ile | Asp | Leu | Gly |     |
| 305 |     |     |     |     | 310 |     |     |     |     | 315 |     |     |     |     | 320 |     |
| gcg | gtt | acc | ggc | atc | ggc | gca | ttc | ggc | tac | att | tac | ggc | acc | aaa | gga | 1008 |
| Ala | Val | Thr | Gly | Ile | Gly | Ala | Phe | Gly | Tyr | Ile | Tyr | Gly | Thr | Lys | Gly |     |
|     |     |     |     | 325 |     |     |     |     | 330 |     |     |     |     | 335 |     |     |
| ttc | caa | gca | ccc | gaa | gta | gcc | acc | cat | ggc | ccc | tca | atc | tcc | tcc | gat | 1056 |
| Phe | Gln | Ala | Pro | Glu | Val | Ala | Thr | His | Gly | Pro | Ser | Ile | Ser | Ser | Asp |     |
|     |     |     | 340 |     |     |     |     | 345 |     |     |     |     | 350 |     |     |     |
| att | ttc | acc | atc | gga | cgc | acc | ctc | gca | gca | ctc | acc | atg | ccc | ctc | ccc | 1104 |
| Ile | Phe | Thr | Ile | Gly | Arg | Thr | Leu | Ala | Ala | Leu | Thr | Met | Pro | Leu | Pro |     |
|     |     | 355 |     |     |     |     | 360 |     |     |     |     | 365 |     |     |     |     |
| gtt | gaa | gac | ggt | gtc | ctc | gca | ccg | ggc | atc | ccc | tcg | ccc | aaa | aat | tca | 1152 |
| Val | Glu | Asp | Gly | Val | Leu | Ala | Pro | Gly | Ile | Pro | Ser | Pro | Lys | Asn | Ser |     |
|     | 370 |     |     |     |     | 375 |     |     |     |     | 380 |     |     |     |     |     |
| cct | ctt | ctg | cgc | agg | cat | ttg | tcg | ttc | tac | cgc | ctc | ctg | caa | cgc | gcc | 1200 |
| Pro | Leu | Leu | Arg | Arg | His | Leu | Ser | Phe | Tyr | Arg | Leu | Leu | Gln | Arg | Ala |     |
| 385 |     |     |     |     | 390 |     |     |     |     | 395 |     |     |     |     | 400 |     |
| acc | gcc | gac | gac | ccc | caa | cac | cga | ttc | cgc | aac | gtc | agc | gaa | cta | cgc | 1248 |
| Thr | Ala | Asp | Asp | Pro | Gln | His | Arg | Phe | Arg | Asn | Val | Ser | Glu | Leu | Arg |     |
|     |     |     |     | 405 |     |     |     |     | 410 |     |     |     |     | 415 |     |     |
| acc | caa | ctc | tac | ggc | gta | ctg | cgt | gaa | att | ttg | gca | gtc | cgc | gac | ggc | 1296 |
| Thr | Gln | Leu | Tyr | Gly | Val | Leu | Arg | Glu | Ile | Leu | Ala | Val | Arg | Asp | Gly |     |
|     |     |     | 420 |     |     |     |     | 425 |     |     |     |     | 430 |     |     |     |

-continued

| | | |
|---|---|---|
| aaa caa tac ccg cca cag cac tca cta ttc tcc cca cag cga agc acc<br>Lys Gln Tyr Pro Pro Gln His Ser Leu Phe Ser Pro Gln Arg Ser Thr<br>435 440 445 | 1344 | |
| ttt ggc acc aaa cac ctc gtg ttc cgc acc gac cgc atc atc gac ggc<br>Phe Gly Thr Lys His Leu Val Phe Arg Thr Asp Arg Ile Ile Asp Gly<br>450 455 460 | 1392 | |
| atc gaa cga caa gca cgc atc aca gca cca gaa att gtc tcc gcg ctg<br>Ile Glu Arg Gln Ala Arg Ile Thr Ala Pro Glu Ile Val Ser Ala Leu<br>465 470 475 480 | 1440 | |
| cct gtc cca ctc atc gac cgc acc gac ccc ggc gcc cgt atg ctc tcc<br>Pro Val Pro Leu Ile Asp Arg Thr Asp Pro Gly Ala Arg Met Leu Ser<br>485 490 495 | 1488 | |
| gga tcc tcc tat gca gaa ccc tcc gaa acc ctg gaa act ctg cgc aac<br>Gly Ser Ser Tyr Ala Glu Pro Ser Glu Thr Leu Glu Thr Leu Arg Asn<br>500 505 510 | 1536 | |
| tcc atg gaa gac gag caa tac cgc caa tca atc gag atc ccc ctc ggt<br>Ser Met Glu Asp Glu Gln Tyr Arg Gln Ser Ile Glu Ile Pro Leu Gly<br>515 520 525 | 1584 | |
| gtc gtc cga gcc ctc ctt gac cta ggc ttt acc acc gaa gca cgc caa<br>Val Val Arg Ala Leu Leu Asp Leu Gly Phe Thr Thr Glu Ala Arg Gln<br>530 535 540 | 1632 | |
| tgg ctc gaa acc cta gag gga cgc atc ggc gac gac tgg cga cac aaa<br>Trp Leu Glu Thr Leu Glu Gly Arg Ile Gly Asp Asp Trp Arg His Lys<br>545 550 555 560 | 1680 | |
| tgg ttc tcc gga atc acc tac ctc ctc ctc gac gac tac gcc acc gcc<br>Trp Phe Ser Gly Ile Thr Tyr Leu Leu Leu Asp Asp Tyr Ala Thr Ala<br>565 570 575 | 1728 | |
| caa gta ttc ttc aac cac gtc ctg acc atc ctg ccc ggc gaa gcc gct<br>Gln Val Phe Phe Asn His Val Leu Thr Ile Leu Pro Gly Glu Ala Ala<br>580 585 590 | 1776 | |
| cct aaa cta gcc ctc gca gct gtt gac gaa ctc atc ctc caa caa atc<br>Pro Lys Leu Ala Leu Ala Ala Val Asp Glu Leu Ile Leu Gln Gln Ile<br>595 600 605 | 1824 | |
| ggc gcc gaa tcc acc gcc tat ctc acc cca gac atc gtc tct gca acc<br>Gly Ala Glu Ser Thr Ala Tyr Leu Thr Pro Asp Ile Val Ser Ala Thr<br>610 615 620 | 1872 | |
| gcg acc ctc agc aaa gat ttc gaa gac ctc gac gcc tcc gcc ttc gaa<br>Ala Thr Leu Ser Lys Asp Phe Glu Asp Leu Asp Ala Ser Ala Phe Glu<br>625 630 635 640 | 1920 | |
| tca ctc agc gac acc tgg tcc cac atc tcc agc gac cca cac gta gtc<br>Ser Leu Ser Asp Thr Trp Ser His Ile Ser Ser Asp Pro His Val Val<br>645 650 655 | 1968 | |
| cgc ttc cat tca ctg cgc ctc tac gca ctt gtc tgg gca acc aac ccc<br>Arg Phe His Ser Leu Arg Leu Tyr Ala Leu Val Trp Ala Thr Asn Pro<br>660 665 670 | 2016 | |
| acc acc gtg tcc tcc gcg ttc ggg ctc gcc cgc caa ctc atg gcc gaa<br>Thr Thr Val Ser Ser Ala Phe Gly Leu Ala Arg Gln Leu Met Ala Glu<br>675 680 685 | 2064 | |
| aac caa atc gaa ctc gca gtc caa gcc cta gac aaa ctc ccc caa tca<br>Asn Gln Ile Glu Leu Ala Val Gln Ala Leu Asp Lys Leu Pro Gln Ser<br>690 695 700 | 2112 | |
| tcc acc cac tac cga atg gcc acc ctc acc acc atc ttg ttg ctg gtc<br>Ser Thr His Tyr Arg Met Ala Thr Leu Thr Thr Ile Leu Leu Leu Val<br>705 710 715 720 | 2160 | |
| agc tcc aat ttg agt gaa tcc cgc atc cga cgg gct gcc cgc cga ctc<br>Ser Ser Asn Leu Ser Glu Ser Arg Ile Arg Arg Ala Ala Arg Arg Leu<br>725 730 735 | 2208 | |
| acc gaa atc ccc aca aac gaa ccc cgc ttc aac caa atc aaa att gcc<br>Thr Glu Ile Pro Thr Asn Glu Pro Arg Phe Asn Gln Ile Lys Ile Ala<br>740 745 750 | 2256 | |

|  |  |  |  |  |  |  |  |  |  |  |  |  |  |  |  | |
|---|---|---|---|---|---|---|---|---|---|---|---|---|---|---|---|---|
| atc | atg | tcg | gca | ggc | ctc | agc | tgg | ctt | cga | gag | cga | aaa | ctc | aaa | gct | 2304 |
| Ile | Met | Ser | Ala | Gly | Leu | Ser | Trp | Leu | Arg | Glu | Arg | Lys | Leu | Lys | Ala | |
|  | 755 |  |  |  | 760 |  |  |  | 765 |  |  |  |  |  |  | |
| tcc | gcc | tcc | gcg | aac | cct | ttg | ttt | gaa | tac | ccg | ttc | tcc | caa | aaa | ggc | 2352 |
| Ser | Ala | Ser | Ala | Asn | Pro | Leu | Phe | Glu | Tyr | Pro | Phe | Ser | Gln | Lys | Gly | |
| 770 |  |  |  | 775 |  |  |  |  | 780 |  |  |  |  |  |  | |
| ctg | cgc | acc | ggc | atc | tcc | gag | gca | ctc | cgc | att | cag | gca | cgt | tct | gca | 2400 |
| Leu | Arg | Thr | Gly | Ile | Ser | Glu | Ala | Leu | Arg | Ile | Gln | Ala | Arg | Ser | Ala | |
| 785 |  |  |  | 790 |  |  |  |  | 795 |  |  |  |  |  | 800 | |
| ccg | ttc | ccg | cac | cac | cgt | tac | gca | ctt | gtg | gat | atg | gcg | aat | gcc | gtg | 2448 |
| Pro | Phe | Pro | His | His | Arg | Tyr | Ala | Leu | Val | Asp | Met | Ala | Asn | Ala | Val | |
|  |  |  |  | 805 |  |  |  |  | 810 |  |  |  |  | 815 |  | |
| cgg | cca | ctg | agt | tgg | ttc |  |  |  |  |  |  |  |  |  |  | 2466 |
| Arg | Pro | Leu | Ser | Trp | Phe |  |  |  |  |  |  |  |  |  |  | |
|  |  |  |  | 820 |  |  |  |  |  |  |  |  |  |  |  | |

<210> SEQ ID NO 20
<211> LENGTH: 822
<212> TYPE: PRT
<213> ORGANISM: Corynebacterium glutamicum

<400> SEQUENCE: 20

Met Lys Asp Asn Glu Asp Phe Asp Pro Asp Ser Pro Ala Thr Glu Ala
1               5                   10                  15

Val Ala Phe Asn Pro Phe Asp Asp Asp Glu Asp Asp Ser Pro Ala
            20                  25                  30

Thr Ser Ala Val Ala Phe Asn Pro Phe Glu Asp Asp Asp Asp Asp
        35                  40                  45

Glu Phe Gln Gly Glu Gly Leu Glu Phe Leu Leu Arg Asp Leu Asp Asn
    50                  55                  60

Leu Arg Ala Thr Gln Gly Gln Met Val Val Gln Pro Ala Val Glu
65                  70                  75                  80

Asp Ser Leu Gly Ser Ala Ser Ala His Thr Glu Thr Thr Ala Ala Ser
                85                  90                  95

Leu Arg Pro Arg Pro Glu Val Asp Pro Ser Glu Arg Ser Arg Arg Gln
            100                 105                 110

Ala Ile Ser Leu Phe Arg Glu Arg Arg Val Arg Gln Ser Arg
        115                 120                 125

Pro Val Ala Asp Gly Met Val Glu Leu Pro Phe Ile Thr Pro Lys Pro
    130                 135                 140

Glu Asp Glu Leu Leu Ile Asp Pro Glu Lys Lys Arg Lys Pro Gly Val
145                 150                 155                 160

Ala Ala Pro Gln Leu Val Ala Gly Asp Ile Val Ala Glu Gln Tyr Glu
                165                 170                 175

Val Leu Gly Val Ile Ala His Gly Gly Met Gly Trp Ile Tyr Leu Ala
            180                 185                 190

Asn Asp Arg Asn Val Ser Gly Arg Ile Val Val Leu Lys Gly Met Met
        195                 200                 205

Ala Gln Ser Ser Val Gln Asp Gln Gly Thr Ala Glu Ala Glu Arg Glu
    210                 215                 220

Phe Leu Ala Asp Ile Thr His Pro Gly Ile Val Lys Ala Tyr Asn Phe
225                 230                 235                 240

Ile Asp Asp Pro Arg Val Pro Gly Gly Phe Ile Val Met Glu Tyr Val
                245                 250                 255

Asn Gly Pro Ser Leu Lys Asp Arg Cys Lys Ala Gln Pro Asp Gly Val
            260                 265                 270

```
Leu Arg Val Asp Leu Ala Ile Gly Tyr Ile Leu Glu Leu Leu Pro Ala
        275                 280                 285

Met Asp Tyr Leu His Gln Arg Gly Val Val Tyr Asn Asp Leu Lys Pro
        290                 295                 300

Glu Asn Val Ile Ala Thr Glu Asp Gln Val Lys Leu Ile Asp Leu Gly
305                 310                 315                 320

Ala Val Thr Gly Ile Gly Ala Phe Gly Tyr Ile Tyr Gly Thr Lys Gly
                325                 330                 335

Phe Gln Ala Pro Glu Val Ala Thr His Gly Pro Ser Ile Ser Ser Asp
            340                 345                 350

Ile Phe Thr Ile Gly Arg Thr Leu Ala Ala Leu Thr Met Pro Leu Pro
        355                 360                 365

Val Glu Asp Gly Val Leu Ala Pro Gly Ile Pro Ser Pro Lys Asn Ser
    370                 375                 380

Pro Leu Leu Arg Arg His Leu Ser Phe Tyr Arg Leu Leu Gln Arg Ala
385                 390                 395                 400

Thr Ala Asp Asp Pro Gln His Arg Phe Arg Asn Val Ser Glu Leu Arg
                405                 410                 415

Thr Gln Leu Tyr Gly Val Leu Arg Glu Ile Leu Ala Val Arg Asp Gly
            420                 425                 430

Lys Gln Tyr Pro Pro Gln His Ser Leu Phe Ser Pro Gln Arg Ser Thr
        435                 440                 445

Phe Gly Thr Lys His Leu Val Phe Arg Thr Asp Arg Ile Ile Asp Gly
    450                 455                 460

Ile Glu Arg Gln Ala Arg Ile Thr Ala Pro Glu Ile Val Ser Ala Leu
465                 470                 475                 480

Pro Val Pro Leu Ile Asp Arg Thr Asp Pro Gly Ala Arg Met Leu Ser
                485                 490                 495

Gly Ser Ser Tyr Ala Glu Pro Ser Glu Thr Leu Glu Thr Leu Arg Asn
            500                 505                 510

Ser Met Glu Asp Glu Gln Tyr Arg Gln Ser Ile Glu Ile Pro Leu Gly
        515                 520                 525

Val Val Arg Ala Leu Leu Asp Leu Gly Phe Thr Thr Glu Ala Arg Gln
    530                 535                 540

Trp Leu Glu Thr Leu Glu Gly Arg Ile Gly Asp Asp Trp Arg His Lys
545                 550                 555                 560

Trp Phe Ser Gly Ile Thr Tyr Leu Leu Leu Asp Asp Tyr Ala Thr Ala
                565                 570                 575

Gln Val Phe Phe Asn His Val Leu Thr Ile Leu Pro Gly Glu Ala Ala
            580                 585                 590

Pro Lys Leu Ala Leu Ala Ala Val Asp Glu Leu Ile Leu Gln Gln Ile
        595                 600                 605

Gly Ala Glu Ser Thr Ala Tyr Leu Thr Pro Asp Ile Val Ser Ala Thr
    610                 615                 620

Ala Thr Leu Ser Lys Asp Phe Glu Asp Leu Asp Ala Ser Ala Phe Glu
625                 630                 635                 640

Ser Leu Ser Asp Thr Trp Ser His Ile Ser Ser Asp Pro His Val Val
                645                 650                 655

Arg Phe His Ser Leu Arg Leu Tyr Ala Leu Val Trp Ala Thr Asn Pro
            660                 665                 670

Thr Thr Val Ser Ser Ala Phe Gly Leu Ala Arg Gln Leu Met Ala Glu
        675                 680                 685
```

```
Asn Gln Ile Glu Leu Ala Val Gln Ala Leu Asp Lys Leu Pro Gln Ser
    690                 695                 700

Ser Thr His Tyr Arg Met Ala Thr Leu Thr Thr Ile Leu Leu Leu Val
705                 710                 715                 720

Ser Ser Asn Leu Ser Glu Ser Arg Ile Arg Arg Ala Ala Arg Arg Leu
                725                 730                 735

Thr Glu Ile Pro Thr Asn Glu Pro Arg Phe Asn Gln Ile Lys Ile Ala
            740                 745                 750

Ile Met Ser Ala Gly Leu Ser Trp Leu Arg Glu Arg Lys Leu Lys Ala
        755                 760                 765

Ser Ala Ser Ala Asn Pro Leu Phe Glu Tyr Pro Phe Ser Gln Lys Gly
770                 775                 780

Leu Arg Thr Gly Ile Ser Glu Ala Leu Arg Ile Gln Ala Arg Ser Ala
785                 790                 795                 800

Pro Phe Pro His His Arg Tyr Ala Leu Val Asp Met Ala Asn Ala Val
                805                 810                 815

Arg Pro Leu Ser Trp Phe
            820
```

```
<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
gcgagccacc caaggtcaaa                                                  20

<210> SEQ ID NO 22
<211> LENGTH: 23
<212> TYPE: DNA
<213> ORGANISM: Corynebacterium glutamicum

<400> SEQUENCE: 22
gcgagccacc caaggtcaaa tgg                                              23

<210> SEQ ID NO 23
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 23
cacccaaggt caaatggtgg                                                  20

<210> SEQ ID NO 24
<211> LENGTH: 23
<212> TYPE: DNA
<213> ORGANISM: Corynebacterium glutamicum

<400> SEQUENCE: 24
cacccaaggt caaatggtgg tgg                                              23

<210> SEQ ID NO 25
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 25
caatcccgcc cagttgctga                                      20

<210> SEQ ID NO 26
<211> LENGTH: 23
<212> TYPE: DNA
<213> ORGANISM: Corynebacterium glutamicum

<400> SEQUENCE: 26
caatcccgcc cagttgctga tgg                                  23

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
caatcttccg ttcaagacca                                      20

<210> SEQ ID NO 28
<211> LENGTH: 23
<212> TYPE: DNA
<213> ORGANISM: Corynebacterium glutamicum

<400> SEQUENCE: 28
caatcttccg ttcaagacca agg                                  23

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
caagttaaac tcatcgacct                                      20

<210> SEQ ID NO 30
<211> LENGTH: 23
<212> TYPE: DNA
<213> ORGANISM: Corynebacterium glutamicum

<400> SEQUENCE: 30
caagttaaac tcatcgacct cgg                                  23

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
caatcaatcg agatccccct                                      20

<210> SEQ ID NO 32
<211> LENGTH: 23
<212> TYPE: DNA
<213> ORGANISM: Corynebacterium glutamicum

<400> SEQUENCE: 32
caatcaatcg agatccccct cgg                                  23

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
gtccgagccc tccttgacct                                                   20

<210> SEQ ID NO 34
<211> LENGTH: 23
<212> TYPE: DNA
<213> ORGANISM: Corynebacterium glutamicum

<400> SEQUENCE: 34
gtccgagccc tccttgacct agg                                               23

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
ccaatggctc gaaaccctag                                                   20

<210> SEQ ID NO 36
<211> LENGTH: 23
<212> TYPE: DNA
<213> ORGANISM: Corynebacterium glutamicum

<400> SEQUENCE: 36
ccaatggctc gaaaccctag agg                                               23

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
caatggctcg aaaccctaga                                                   20

<210> SEQ ID NO 38
<211> LENGTH: 23
<212> TYPE: DNA
<213> ORGANISM: Corynebacterium glutamicum

<400> SEQUENCE: 38
caatggctcg aaaccctaga ggg                                               23

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
tggcgacaca aatggttctc                                                   20

<210> SEQ ID NO 40
<211> LENGTH: 23
<212> TYPE: DNA
<213> ORGANISM: Corynebacterium glutamicum

<400> SEQUENCE: 40
tggcgacaca aatggttctc cgg                                              23

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
atgaaggata atgaagattt cgatccagat tcac                                  34

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
gaaccaactc agtggccgc                                                   19

<210> SEQ ID NO 43
<211> LENGTH: 2265
<212> TYPE: DNA
<213> ORGANISM: Brevibacillus choshinensis
<220> FEATURE:
<221> NAME/KEY: CDS
<222> LOCATION: (1)..(2265)

<400> SEQUENCE: 43

| gtg | aac | gca | gtg | aag | aaa | ggc | aag | aag | cta | tta | tcc | atc | cta | ttt | tct | 48 |
|---|---|---|---|---|---|---|---|---|---|---|---|---|---|---|---|---|
| Met | Asn | Ala | Val | Lys | Lys | Gly | Lys | Lys | Leu | Leu | Ser | Ile | Leu | Phe | Ser | |
| 1 | | | | 5 | | | | | 10 | | | | | 15 | | |

| tcc | tca | ctg | gtc | ctg | agc | ggc | att | gcg | gcg | gtt | cca | gcg | aca | ggg | atg | 96 |
|---|---|---|---|---|---|---|---|---|---|---|---|---|---|---|---|---|
| Ser | Ser | Leu | Val | Leu | Ser | Gly | Ile | Ala | Ala | Val | Pro | Ala | Thr | Gly | Met | |
| | | | 20 | | | | | 25 | | | | | 30 | | | |

| gcc | aag | tca | aag | gac | aag | ccg | ccg | ctt | gaa | gtg | gat | ttg | tcc | aca | gtg | 144 |
|---|---|---|---|---|---|---|---|---|---|---|---|---|---|---|---|---|
| Ala | Lys | Ser | Lys | Asp | Lys | Pro | Pro | Leu | Glu | Val | Asp | Leu | Ser | Thr | Val | |
| | | 35 | | | | | 40 | | | | | 45 | | | | |

| aac | atg | gat | cgt | ttg | gtt | aaa | gcc | ttg | atc | gac | caa | ggt | gaa | atc | gac | 192 |
|---|---|---|---|---|---|---|---|---|---|---|---|---|---|---|---|---|
| Asn | Met | Asp | Arg | Leu | Val | Lys | Ala | Leu | Ile | Asp | Gln | Gly | Glu | Ile | Asp | |
| 50 | | | | | 55 | | | | | 60 | | | | | | |

| gag | gac | gcc | gac | cag | gaa | gag | atc | aac | aaa | gct | gtg | gag | aag | ttt | ttg | 240 |
|---|---|---|---|---|---|---|---|---|---|---|---|---|---|---|---|---|
| Glu | Asp | Ala | Asp | Gln | Glu | Glu | Ile | Asn | Lys | Ala | Val | Glu | Lys | Phe | Leu | |
| 65 | | | | 70 | | | | | 75 | | | | | 80 | | |

| aga | gac | aag | aaa | gtt | ccc | cac | ggc | att | gat | gac | tcc | agc | tcc | ttc | ggg | 288 |
|---|---|---|---|---|---|---|---|---|---|---|---|---|---|---|---|---|
| Arg | Asp | Lys | Lys | Val | Pro | His | Gly | Ile | Asp | Asp | Ser | Ser | Ser | Phe | Gly | |
| | | | | 85 | | | | | 90 | | | | | 95 | | |

| aaa | aaa | gca | agc | aaa | acc | cag | ctt | tcg | gca | gta | tca | aag | gca | gca | agc | 336 |
|---|---|---|---|---|---|---|---|---|---|---|---|---|---|---|---|---|
| Lys | Lys | Ala | Ser | Lys | Thr | Gln | Leu | Ser | Ala | Val | Ser | Lys | Ala | Ala | Ser | |
| | | | | 100 | | | | | 105 | | | | | 110 | | |

| aaa | gta | tcc | aag | ctc | aaa | gat | gac | aag | caa | gtg | cgc | gct | tcc | aag | cgg | 384 |
|---|---|---|---|---|---|---|---|---|---|---|---|---|---|---|---|---|
| Lys | Val | Ser | Lys | Leu | Lys | Asp | Asp | Lys | Gln | Val | Arg | Ala | Ser | Lys | Arg | |
| | | | 115 | | | | | 120 | | | | | 125 | | | |

| gta | cat | acg | gat | aat | ctg | gtg | att | gcc | ctg | gtc | gag | ttc | aat | gat | ctg | 432 |
|---|---|---|---|---|---|---|---|---|---|---|---|---|---|---|---|---|
| Val | His | Thr | Asp | Asn | Leu | Val | Ile | Ala | Leu | Val | Glu | Phe | Asn | Asp | Leu | |

-continued

```
            130                 135                 140
gag cac aac cag gtg cca aaa caa agc gat tcc ttg tgg acg gca gac       480
Glu His Asn Gln Val Pro Lys Gln Ser Asp Ser Leu Trp Thr Ala Asp
145                 150                 155                 160 ttc gac caa aag cac tac gag gaa atg ctg ttc gat cgt aaa ggc tat       528
Phe Asp Gln Lys His Tyr Glu Glu Met Leu Phe Asp Arg Lys Gly Tyr
                165                 170                 175 acg act cct gaa ggg ata agc atg acc acg atg gcc aag tac tac tac       576
Thr Thr Pro Glu Gly Ile Ser Met Thr Thr Met Ala Lys Tyr Tyr Tyr
            180                 185                 190 gag caa tcg ggt gag aca tgg acc gtg gat ggg gtt gtc act ccg tgg       624
Glu Gln Ser Gly Glu Thr Trp Thr Val Asp Gly Val Val Thr Pro Trp
        195                 200                 205 ttg act gcc gaa aaa gat aag aaa ttc tac ggt gga aac gat gaa aac       672
Leu Thr Ala Glu Lys Asp Lys Lys Phe Tyr Gly Gly Asn Asp Glu Asn
210                 215                 220 ggc aac gat gcc aac cca cgc gat ctg gtc gtc gag aca ctg gaa tct       720
Gly Asn Asp Ala Asn Pro Arg Asp Leu Val Val Glu Thr Leu Glu Ser
225                 230                 235                 240 gta ggg gat gcc atc aag ggt cat gaa gaa gaa tac gac caa cgc gac       768
Val Gly Asp Ala Ile Lys Gly His Glu Glu Glu Tyr Asp Gln Arg Asp
                245                 250                 255 ccg tat gac ttg gat gga gac agc gat ctg atg gag ccg gat ggc atg       816
Pro Tyr Asp Leu Asp Gly Asp Ser Asp Leu Met Glu Pro Asp Gly Met
            260                 265                 270 ctg gac aac ctg atg ctg gtt cac tcc ggt att ggt gaa gag act ggg       864
Leu Asp Asn Leu Met Leu Val His Ser Gly Ile Gly Glu Glu Thr Gly
        275                 280                 285 gaa gat gcg gat gcg atc tgg tct cac cgc tgg act ctg aaa aag ccg       912
Glu Asp Ala Asp Ala Ile Trp Ser His Arg Trp Thr Leu Lys Lys Pro
290                 295                 300 aca gaa att cca ggc acc agc ctg aaa gct tac gac tac atg att cag       960
Thr Glu Ile Pro Gly Thr Ser Leu Lys Ala Tyr Asp Tyr Met Ile Gln
305                 310                 315                 320 cct gaa gat ggc gca ccc ggc gta ttc gca cat gaa tac gga cac aac      1008
Pro Glu Asp Gly Ala Pro Gly Val Phe Ala His Glu Tyr Gly His Asn
                325                 330                 335 ctg gga ctg cca gat ctg tat gac acg aca aga ctg gga cat gat tcg      1056
Leu Gly Leu Pro Asp Leu Tyr Asp Thr Thr Arg Leu Gly His Asp Ser
            340                 345                 350 ccg gtt ggc gca tgg tcg ctg atg tct tcc gga agc cat aca ggt aag      1104
Pro Val Gly Ala Trp Ser Leu Met Ser Ser Gly Ser His Thr Gly Lys
        355                 360                 365 atc ttc caa acc caa cca acc gga ttt gat cct tgg tcc aaa atg atg      1152
Ile Phe Gln Thr Gln Pro Thr Gly Phe Asp Pro Trp Ser Lys Met Met
370                 375                 380 ctg cag gaa atg tat ggg ggc aag tgg att gag ccg caa gtc atc aat      1200
Leu Gln Glu Met Tyr Gly Gly Lys Trp Ile Glu Pro Gln Val Ile Asn
385                 390                 395                 400 tac gaa gac ctg aaa aaa cgg aaa aag cag gct tcg ctc tac gat ggc      1248
Tyr Glu Asp Leu Lys Lys Arg Lys Lys Gln Ala Ser Leu Tyr Asp Gly
                405                 410                 415 agc agc ctc gat gaa gat ggc aaa gtc atc aag ctg aat atg ccg caa      1296
Ser Ser Leu Asp Glu Asp Gly Lys Val Ile Lys Leu Asn Met Pro Gln
            420                 425                 430 gta gag aag aca ccg ccg gtt caa ccg aaa gac ggc gat tat tct tac      1344
Val Glu Lys Thr Pro Pro Val Gln Pro Lys Asp Gly Asp Tyr Ser Tyr
        435                 440                 445 ttc tcc gat gag ggc gac aat ctg aac acg aag atg act tcg gaa gtg      1392
```

```
                Phe Ser Asp Glu Gly Asp Asn Leu Asn Thr Lys Met Thr Ser Glu Val
                    450                 455                 460 atc gac ctg aca ggc gcc agc tcc gca tcg atg agc ttc gac tcc tgg         1440
Ile Asp Leu Thr Gly Ala Ser Ser Ala Ser Met Ser Phe Asp Ser Trp
465                 470                 475                 480 aga gcg atc gag acc ggg tac gac tac ctg tac gtg aac gtg att gat         1488
Arg Ala Ile Glu Thr Gly Tyr Asp Tyr Leu Tyr Val Asn Val Ile Asp
                485                 490                 495 gtc gac tca ggt gag agc aca aca gta aaa gag tac gat gac gaa acc         1536
Val Asp Ser Gly Glu Ser Thr Thr Val Lys Glu Tyr Asp Asp Glu Thr
            500                 505                 510 aaa ggc tgg gat aag gaa gaa atc agc ctg aac gat ttc gct ggc aaa         1584
Lys Gly Trp Asp Lys Glu Glu Ile Ser Leu Asn Asp Phe Ala Gly Lys
        515                 520                 525 aag att caa gtc gag ttc aac tac gtg acg gat ggc ggc ttg gcg atg         1632
Lys Ile Gln Val Glu Phe Asn Tyr Val Thr Asp Gly Gly Leu Ala Met
    530                 535                 540 tcc ggc ttc tat ctg gat aat ttt gca gtc aca gca gac ggc gaa gta         1680
Ser Gly Phe Tyr Leu Asp Asn Phe Ala Val Thr Ala Asp Gly Glu Val
545                 550                 555                 560 gtc ttc tcg gat gat gca gaa ggc gac cag aag ttt gat ctg gat gga         1728
Val Phe Ser Asp Asp Ala Glu Gly Asp Gln Lys Phe Asp Leu Asp Gly
                565                 570                 575 ttc atc cat ttc gac ggc gaa ggc aaa atg tac gac gcg tac tac ctg         1776
Phe Ile His Phe Asp Gly Glu Gly Lys Met Tyr Asp Ala Tyr Tyr Leu
            580                 585                 590 gta gag ctg cgc tcc cat gaa ggc gtg gac gag ggt ctg aaa tac ttc         1824
Val Glu Leu Arg Ser His Glu Gly Val Asp Glu Gly Leu Lys Tyr Phe
        595                 600                 605 cgc cgc aat gac aca ttc ttc acg tat gat cca ggt ctg gtg atc tgg         1872
Arg Arg Asn Asp Thr Phe Phe Thr Tyr Asp Pro Gly Leu Val Ile Trp
    610                 615                 620 tac tac gat gga cgc ttt ggc aaa acg caa gac aac aac acc agc aac         1920
Tyr Tyr Asp Gly Arg Phe Gly Lys Thr Gln Asp Asn Asn Thr Ser Asn
625                 630                 635                 640 cat cca ggc tac ggc atg ctg ggc gta gtc gat gcg cat cag gaa gtt         1968
His Pro Gly Tyr Gly Met Leu Gly Val Val Asp Ala His Gln Glu Val
                645                 650                 655 cgt tac tgg aat aac gat gag ggc aac gag gag gcc att gcc gac tcc         2016
Arg Tyr Trp Asn Asn Asp Glu Gly Asn Glu Glu Ala Ile Ala Asp Ser
            660                 665                 670 cgt tac caa gtg aac gat gcg gca ttc agc ccg aac aaa acc tcc ggc         2064
Arg Tyr Gln Val Asn Asp Ala Ala Phe Ser Pro Asn Lys Thr Ser Gly
        675                 680                 685 atg gat ctc gac tac att ctc ggc acg atg gat tac gag ccg ctg aaa         2112
Met Asp Leu Asp Tyr Ile Leu Gly Thr Met Asp Tyr Glu Pro Leu Lys
    690                 695                 700 ggc att acc gta ttc aaa gac agt gat gat tac acg atg ccg gaa gtt         2160
Gly Ile Thr Val Phe Lys Asp Ser Asp Asp Tyr Thr Met Pro Glu Val
705                 710                 715                 720 ccg gaa atc gga aaa atc ctg ccg aag atc ggt ctg caa atc aaa tta         2208
Pro Glu Ile Gly Lys Ile Leu Pro Lys Ile Gly Leu Gln Ile Lys Leu
                725                 730                 735 att cgt gtg tcc aag aaa ttc acg aac gca cag gtc gag ttc tcc atc         2256
Ile Arg Val Ser Lys Lys Phe Thr Asn Ala Gln Val Glu Phe Ser Ile
            740                 745                 750 aaa aaa taa                                                              2265
Lys Lys
```

<210> SEQ ID NO 44
<211> LENGTH: 754
<212> TYPE: PRT
<213> ORGANISM: Brevibacillus choshinensis

<400> SEQUENCE: 44

| | | | | | | | | | | | | | | |
|---|---|---|---|---|---|---|---|---|---|---|---|---|---|---|
| Met | Asn | Ala | Val | Lys | Lys | Gly | Lys | Lys | Leu | Leu | Ser | Ile | Leu | Phe | Ser |
| 1 | | | | 5 | | | | | 10 | | | | | 15 | |
| Ser | Ser | Leu | Val | Leu | Ser | Gly | Ile | Ala | Ala | Val | Pro | Ala | Thr | Gly | Met |
| | | | 20 | | | | | 25 | | | | | 30 | | |
| Ala | Lys | Ser | Lys | Asp | Lys | Pro | Pro | Leu | Glu | Val | Asp | Leu | Ser | Thr | Val |
| | | 35 | | | | | 40 | | | | | 45 | | | |
| Asn | Met | Asp | Arg | Leu | Val | Lys | Ala | Leu | Ile | Asp | Gln | Gly | Glu | Ile | Asp |
| 50 | | | | | 55 | | | | | 60 | | | | | |
| Glu | Asp | Ala | Asp | Gln | Glu | Glu | Ile | Asn | Lys | Ala | Val | Glu | Lys | Phe | Leu |
| 65 | | | | | 70 | | | | | 75 | | | | | 80 |
| Arg | Asp | Lys | Lys | Val | Pro | His | Gly | Ile | Asp | Asp | Ser | Ser | Ser | Phe | Gly |
| | | | | 85 | | | | | 90 | | | | | 95 | |
| Lys | Lys | Ala | Ser | Lys | Thr | Gln | Leu | Ser | Ala | Val | Ser | Lys | Ala | Ala | Ser |
| | | | 100 | | | | | 105 | | | | | 110 | | |
| Lys | Val | Ser | Lys | Leu | Lys | Asp | Asp | Lys | Gln | Val | Arg | Ala | Ser | Lys | Arg |
| | | 115 | | | | | 120 | | | | | 125 | | | |
| Val | His | Thr | Asp | Asn | Leu | Val | Ile | Ala | Leu | Val | Glu | Phe | Asn | Asp | Leu |
| 130 | | | | | 135 | | | | | 140 | | | | | |
| Glu | His | Asn | Gln | Val | Pro | Lys | Gln | Ser | Asp | Ser | Leu | Trp | Thr | Ala | Asp |
| 145 | | | | | 150 | | | | | 155 | | | | | 160 |
| Phe | Asp | Gln | Lys | His | Tyr | Glu | Glu | Met | Leu | Phe | Asp | Arg | Lys | Gly | Tyr |
| | | | | 165 | | | | | 170 | | | | | 175 | |
| Thr | Thr | Pro | Glu | Gly | Ile | Ser | Met | Thr | Thr | Met | Ala | Lys | Tyr | Tyr | Tyr |
| | | | 180 | | | | | 185 | | | | | 190 | | |
| Glu | Gln | Ser | Gly | Glu | Thr | Trp | Thr | Val | Asp | Gly | Val | Val | Thr | Pro | Trp |
| | | | 195 | | | | | 200 | | | | | 205 | | |
| Leu | Thr | Ala | Glu | Lys | Asp | Lys | Lys | Phe | Tyr | Gly | Gly | Asn | Asp | Glu | Asn |
| 210 | | | | | 215 | | | | | 220 | | | | | |
| Gly | Asn | Asp | Ala | Asn | Pro | Arg | Asp | Leu | Val | Val | Glu | Thr | Leu | Glu | Ser |
| 225 | | | | | 230 | | | | | 235 | | | | | 240 |
| Val | Gly | Asp | Ala | Ile | Lys | Gly | His | Glu | Glu | Tyr | Asp | Gln | Arg | Asp |
| | | | | 245 | | | | | 250 | | | | | 255 | |
| Pro | Tyr | Asp | Leu | Asp | Gly | Asp | Ser | Asp | Leu | Met | Glu | Pro | Asp | Gly | Met |
| | | | 260 | | | | | 265 | | | | | 270 | | |
| Leu | Asp | Asn | Leu | Met | Leu | Val | His | Ser | Gly | Ile | Gly | Glu | Glu | Thr | Gly |
| | | 275 | | | | | 280 | | | | | 285 | | | |
| Glu | Asp | Ala | Asp | Ala | Ile | Trp | Ser | His | Arg | Trp | Thr | Leu | Lys | Lys | Pro |
| 290 | | | | | 295 | | | | | 300 | | | | | |
| Thr | Glu | Ile | Pro | Gly | Thr | Ser | Leu | Lys | Ala | Tyr | Asp | Tyr | Met | Ile | Gln |
| 305 | | | | | 310 | | | | | 315 | | | | | 320 |
| Pro | Glu | Asp | Gly | Ala | Pro | Gly | Val | Phe | Ala | His | Glu | Tyr | Gly | His | Asn |
| | | | | 325 | | | | | 330 | | | | | 335 | |
| Leu | Gly | Leu | Pro | Asp | Leu | Tyr | Asp | Thr | Thr | Arg | Leu | Gly | His | Asp | Ser |
| | | | 340 | | | | | 345 | | | | | 350 | | |
| Pro | Val | Gly | Ala | Trp | Ser | Leu | Met | Ser | Ser | Gly | Ser | His | Thr | Gly | Lys |
| | | 355 | | | | | 360 | | | | | 365 | | | |
| Ile | Phe | Gln | Thr | Gln | Pro | Thr | Gly | Phe | Asp | Pro | Trp | Ser | Lys | Met | Met |
| 370 | | | | | 375 | | | | | 380 | | | | | |

Leu Gln Glu Met Tyr Gly Gly Lys Trp Ile Glu Pro Gln Val Ile Asn
385                 390                 395                 400

Tyr Glu Asp Leu Lys Lys Arg Lys Lys Gln Ala Ser Leu Tyr Asp Gly
            405                 410                 415

Ser Ser Leu Asp Glu Asp Gly Lys Val Ile Lys Leu Asn Met Pro Gln
            420                 425                 430

Val Glu Lys Thr Pro Pro Val Gln Pro Lys Asp Gly Asp Tyr Ser Tyr
            435                 440                 445

Phe Ser Asp Glu Gly Asp Asn Leu Asn Thr Lys Met Thr Ser Glu Val
    450                 455                 460

Ile Asp Leu Thr Gly Ala Ser Ser Ala Ser Met Ser Phe Asp Ser Trp
465                 470                 475                 480

Arg Ala Ile Glu Thr Gly Tyr Asp Tyr Leu Tyr Val Asn Val Ile Asp
                485                 490                 495

Val Asp Ser Gly Glu Ser Thr Thr Val Lys Glu Tyr Asp Asp Glu Thr
            500                 505                 510

Lys Gly Trp Asp Lys Glu Glu Ile Ser Leu Asn Asp Phe Ala Gly Lys
            515                 520                 525

Lys Ile Gln Val Glu Phe Asn Tyr Val Thr Asp Gly Gly Leu Ala Met
            530                 535                 540

Ser Gly Phe Tyr Leu Asp Asn Phe Ala Val Thr Ala Asp Gly Glu Val
545                 550                 555                 560

Val Phe Ser Asp Asp Ala Glu Gly Asp Gln Lys Phe Asp Leu Asp Gly
                565                 570                 575

Phe Ile His Phe Asp Gly Glu Gly Lys Met Tyr Asp Ala Tyr Tyr Leu
            580                 585                 590

Val Glu Leu Arg Ser His Glu Gly Val Asp Glu Gly Leu Lys Tyr Phe
            595                 600                 605

Arg Arg Asn Asp Thr Phe Phe Thr Tyr Asp Pro Gly Leu Val Ile Trp
610                 615                 620

Tyr Tyr Asp Gly Arg Phe Gly Lys Thr Gln Asp Asn Asn Thr Ser Asn
625                 630                 635                 640

His Pro Gly Tyr Gly Met Leu Gly Val Val Asp Ala His Gln Glu Val
                645                 650                 655

Arg Tyr Trp Asn Asn Asp Glu Gly Asn Glu Glu Ala Ile Ala Asp Ser
            660                 665                 670

Arg Tyr Gln Val Asn Asp Ala Ala Phe Ser Pro Asn Lys Thr Ser Gly
            675                 680                 685

Met Asp Leu Asp Tyr Ile Leu Gly Thr Met Asp Tyr Glu Pro Leu Lys
690                 695                 700

Gly Ile Thr Val Phe Lys Asp Ser Asp Asp Tyr Thr Met Pro Glu Val
705                 710                 715                 720

Pro Glu Ile Gly Lys Ile Leu Pro Lys Ile Gly Leu Gln Ile Lys Leu
                725                 730                 735

Ile Arg Val Ser Lys Lys Phe Thr Asn Ala Gln Val Glu Phe Ser Ile
            740                 745                 750

Lys Lys

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
agcaagtgcg cgcttccaag    20

<210> SEQ ID NO 46
<211> LENGTH: 30
<212> TYPE: DNA
<213> ORGANISM: Brevibacillus choshinensis

<400> SEQUENCE: 46
gatgacaagc aagtgcgcgc ttccaagcgg    30

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
gcaagtgcgc gcttccaagc    20

<210> SEQ ID NO 48
<211> LENGTH: 30
<212> TYPE: DNA
<213> ORGANISM: Brevibacillus choshinensis

<400> SEQUENCE: 48
atgacaagca agtgcgcgct tccaagcggg    30

<210> SEQ ID NO 49
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 49
acaaagcgat tccttgtgga    20

<210> SEQ ID NO 50
<211> LENGTH: 30
<212> TYPE: DNA
<213> ORGANISM: Brevibacillus choshinensis

<400> SEQUENCE: 50
tgccaaaaca aagcgattcc ttgtggacgg    30

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
cagcctgaag atggcgcacc    20

<210> SEQ ID NO 52
<211> LENGTH: 30
<212> TYPE: DNA
<213> ORGANISM: Brevibacillus choshinensis

<400> SEQUENCE: 52
catgattcag cctgaagatg gcgcacccgg    30

<210> SEQ ID NO 53
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 53
aagcaggctt cgctctacga                                           20

<210> SEQ ID NO 54
<211> LENGTH: 30
<212> TYPE: DNA
<213> ORGANISM: Brevibacillus choshinensis

<400> SEQUENCE: 54
acggaaaaag caggcttcgc tctacgatgg                                30

<210> SEQ ID NO 55
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 55
gcaagtagag aagacaccgc                                           20

<210> SEQ ID NO 56
<211> LENGTH: 30
<212> TYPE: DNA
<213> ORGANISM: Brevibacillus choshinensis

<400> SEQUENCE: 56
atatgccgca agtagagaag acaccgccgg                                30

<210> SEQ ID NO 57
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 57
gaccagaagt ttgatctgga                                           20

<210> SEQ ID NO 58
<211> LENGTH: 30
<212> TYPE: DNA
<213> ORGANISM: Brevibacillus choshinensis

<400> SEQUENCE: 58
agaaggcgac cagaagtttg atctggatgg                                30

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
gggacatgat tcgccggttg                                           20

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
gcgtccatcg tagtaccaga tc                                          22

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
ccgatagcta agcctattga g                                           21

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
tcatcctgtg gagcttagta g                                           21

<210> SEQ ID NO 63
<211> LENGTH: 909
<212> TYPE: DNA
<213> ORGANISM: Clostridium saccharoperbutylacetonicum
<220> FEATURE:
<221> NAME/KEY: CDS
<222> LOCATION: (1)..(909)

<400> SEQUENCE: 63

```
atg agc aaa aac ttt gac gat tta tta gca aga tta aag gaa gtt cca      48
Met Ser Lys Asn Phe Asp Asp Leu Leu Ala Arg Leu Lys Glu Val Pro
1               5                   10                  15 aca aag aaa gtg gca gtg gca gtg gca cag gac gag cct gta tta gaa      96
Thr Lys Lys Val Ala Val Ala Val Ala Gln Asp Glu Pro Val Leu Glu
                20                  25                  30 gct att aaa gaa gct aca gac aaa aat ata gct caa gct ata ttg gtt     144
Ala Ile Lys Glu Ala Thr Asp Lys Asn Ile Ala Gln Ala Ile Leu Val
            35                  40                  45 gga gat aag caa aaa ata caa gaa ata gca aaa aag ata gac tta gat     192
Gly Asp Lys Gln Lys Ile Gln Glu Ile Ala Lys Lys Ile Asp Leu Asp
        50                  55                  60 tta tca aac tat gaa ata atg gat att gca gat cct aag aaa gct acc     240
Leu Ser Asn Tyr Glu Ile Met Asp Ile Ala Asp Pro Lys Lys Ala Thr
65                  70                  75                  80 tta gaa gca gta aaa tta gtt tca agc ggt cat gca gac atg tta atg     288
Leu Glu Ala Val Lys Leu Val Ser Ser Gly His Ala Asp Met Leu Met
                85                  90                  95 aaa ggt tta gtt gat act gct aca ttt tta aga agc gta tta aat aag     336
Lys Gly Leu Val Asp Thr Ala Thr Phe Leu Arg Ser Val Leu Asn Lys
                100                 105                 110 gaa gtt gga tta aga aca gga aag tta atg tca cac gtt gca gtg ttt     384
Glu Val Gly Leu Arg Thr Gly Lys Leu Met Ser His Val Ala Val Phe
            115                 120                 125
```

```
gat att gaa ggt tgg gat aga cta tta ttt tta aca gat gca gcc ttt    432
Asp Ile Glu Gly Trp Asp Arg Leu Leu Phe Leu Thr Asp Ala Ala Phe
    130                 135                 140 aat aca tat cca gaa tta aag gat aaa gtt gga atg att aat aat gca    480
Asn Thr Tyr Pro Glu Leu Lys Asp Lys Val Gly Met Ile Asn Asn Ala
145                 150                 155                 160 gtt gta gtt gca cat gct tgt gga ata gat gtt cct aag gta gca tct    528
Val Val Val Ala His Ala Cys Gly Ile Asp Val Pro Lys Val Ala Ser
                165                 170                 175 ata tgc cca gta gaa gta gtg aat aca agt atg cct tca act gta gat    576
Ile Cys Pro Val Glu Val Val Asn Thr Ser Met Pro Ser Thr Val Asp
            180                 185                 190 gca gca tta tta gca aaa atg agt gat aga gga caa ttt aaa ggt tgt    624
Ala Ala Leu Leu Ala Lys Met Ser Asp Arg Gly Gln Phe Lys Gly Cys
        195                 200                 205 ata gtt gat gga cct ttt gct tta gat aat gca ata tca gaa gaa gca    672
Ile Val Asp Gly Pro Phe Ala Leu Asp Asn Ala Ile Ser Glu Glu Ala
    210                 215                 220 gct cat cat aaa ggt gtt aca gga aat gtt gca ggt aaa gca gat gta    720
Ala His His Lys Gly Val Thr Gly Asn Val Ala Gly Lys Ala Asp Val
225                 230                 235                 240 tta tta tta cca aat ata gaa aca gca aat gtt atg tat aaa aca tta    768
Leu Leu Leu Pro Asn Ile Glu Thr Ala Asn Val Met Tyr Lys Thr Leu
                245                 250                 255 aca tat ttc tct aaa tca aga aat ggt gga tta tta gtg gga aca tca    816
Thr Tyr Phe Ser Lys Ser Arg Asn Gly Gly Leu Leu Val Gly Thr Ser
            260                 265                 270 gca cca gtt atc tta act tca aga gca gat tct ttt gaa aca aaa gtt    864
Ala Pro Val Ile Leu Thr Ser Arg Ala Asp Ser Phe Glu Thr Lys Val
        275                 280                 285 aac tct att gct tta gca gca tta gtt gca gca aaa aat aag taa        909
Asn Ser Ile Ala Leu Ala Ala Leu Val Ala Ala Lys Asn Lys
    290                 295                 300

<210> SEQ ID NO 64
<211> LENGTH: 302
<212> TYPE: PRT
<213> ORGANISM: Clostridium saccharoperbutylacetonicum

<400> SEQUENCE: 64

Met Ser Lys Asn Phe Asp Asp Leu Leu Ala Arg Leu Lys Glu Val Pro
1               5                   10                  15

Thr Lys Lys Val Ala Val Ala Val Ala Gln Asp Glu Pro Val Leu Glu
                20                  25                  30

Ala Ile Lys Glu Ala Thr Asp Lys Asn Ile Ala Gln Ala Ile Leu Val
            35                  40                  45

Gly Asp Lys Gln Lys Ile Gln Glu Ile Ala Lys Ile Asp Leu Asp
        50                  55                  60

Leu Ser Asn Tyr Glu Ile Met Asp Ile Ala Asp Pro Lys Lys Ala Thr
65                  70                  75                  80

Leu Glu Ala Val Lys Leu Val Ser Ser Gly His Ala Asp Met Leu Met
                85                  90                  95

Lys Gly Leu Val Asp Thr Ala Thr Phe Leu Arg Ser Val Leu Asn Lys
            100                 105                 110

Glu Val Gly Leu Arg Thr Gly Lys Leu Met Ser His Val Ala Val Phe
        115                 120                 125

Asp Ile Glu Gly Trp Asp Arg Leu Leu Phe Leu Thr Asp Ala Ala Phe
    130                 135                 140
```

```
Asn Thr Tyr Pro Glu Leu Lys Asp Lys Val Gly Met Ile Asn Asn Ala
145                 150                 155                 160

Val Val Val Ala His Ala Cys Gly Ile Asp Val Pro Lys Val Ala Ser
                165                 170                 175

Ile Cys Pro Val Glu Val Val Asn Thr Ser Met Pro Ser Thr Val Asp
            180                 185                 190

Ala Ala Leu Leu Ala Lys Met Ser Asp Arg Gly Gln Phe Lys Gly Cys
        195                 200                 205

Ile Val Asp Gly Pro Phe Ala Leu Asp Asn Ala Ile Ser Glu Glu Ala
    210                 215                 220

Ala His His Lys Gly Val Thr Gly Asn Val Ala Gly Lys Ala Asp Val
225                 230                 235                 240

Leu Leu Leu Pro Asn Ile Glu Thr Ala Asn Val Met Tyr Lys Thr Leu
                245                 250                 255

Thr Tyr Phe Ser Lys Ser Arg Asn Gly Gly Leu Leu Val Gly Thr Ser
                260                 265                 270

Ala Pro Val Ile Leu Thr Ser Arg Ala Asp Ser Phe Glu Thr Lys Val
            275                 280                 285

Asn Ser Ile Ala Leu Ala Ala Leu Val Ala Ala Lys Asn Lys
    290                 295                 300
```

```
<210> SEQ ID NO 65
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 65
gccactgcca ctttctttgt                                               20

<210> SEQ ID NO 66
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 66
ccagaattaa aggataaagt                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 67
attgcattat ctaaagcaaa                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 68
acatttgctg tttctatatt                                               20
```

```
<210> SEQ ID NO 69
<211> LENGTH: 26
<212> TYPE: DNA
<213> ORGANISM: Artificial Sequence
<220> FEATURE:
<223> OTHER INFORMATION: Primer

<400> SEQUENCE: 69
gcaagaaatg agcaaaaact ttgacg                                    26

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
gctgcaacta atgctgctaa agc                                       23

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ctctgactgt gcagttaacc                                           20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
cagcaaccga agctgttgcc                                           20

<210> SEQ ID NO 73
<211> LENGTH: 18
<212> TYPE: DNA
<213> ORGANISM: Artificial Sequence
<220> FEATURE:
<223> OTHER INFORMATION: Primer

<400> SEQUENCE: 73
gccatcagca actgggcg                                             18

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
ccggaagcca tacaggtaag atc                                       23

<210> SEQ ID NO 75
<211> LENGTH: 24
<212> TYPE: DNA
<213> ORGANISM: Artificial Sequence
<220> FEATURE:
<223> OTHER INFORMATION: Primer
```

```
<400> SEQUENCE: 75
cctgagtcga catcaatcac gttc                                              24
```

METHOD FOR CONVERTING GENOME SEQUENCE OF GRAM-POSITIVE BACTERIUM BY SPECIFICALLY CONVERTING NUCLEIC ACID BASE OF TARGETED DNA SEQUENCE, AND MOLECULAR COMPLEX USED IN SAME

CROSS-REFERENCE TO RELATED APPLICATIONS

This patent application is the U.S. national phase of International Patent Application No. PCT/JP2016/076711, filed Sep. 9, 2016, which claims the benefit of Japanese Patent Application No. 2015-178022, filed on Sep. 9, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 91,045 bytes ASCII (Text) file named "738491Replacement-SequenceListing.txt," created Oct. 2, 2018.

TECHNICAL FIELD

The present invention relates to a modification method of a genome sequence, which enables modification of a nucleic acid base in a particular region of a genome of gram-positive bacterium, without cleaving double-stranded DNA (no cleavage or single strand cleavage), or inserting a foreign DNA fragment, and a complex of a nucleic acid sequence-recognizing module and a nucleic acid base converting enzyme to be used therefor.

Background Art

Gram-positive bacterium is a generic name for bacteria that are stained in iron blue or purple by gram-staining and includes many useful bacteria such as lactobacillus, actinomycetes and the like utilized in traditional fermentation production and new biotechnology. Unlike gram negative bacteria such as *Escherichia coli* and the like, they do not have an outer membrane. Thus, they have high secretional ability on proteins and the like. In addition, since they do not produce endotoxin, they are also suitable for the production of heterologous proteins. For this reason, many attempts have been made to further improve the properties of useful bacteria by modifying the genes of gram-positive bacteria.

For example, certain kinds of bacteria of the genus *Clostridium* (e.g., *Clostridium saccharoperbutylacetonicum* etc.) have long been utilized as industrial butanol-fermenting bacteria. To improve butanol yield, studies are ongoing with the aim to reduce by-products (acetone, ethanol, organic acid and the like) by gene recombination.

*Corynebacterium glutamicum* has been used for more than 50 years as a bacterium for industrial production of amino acids, including glutamic acid and lysine, for food, feed or medicine. The production of glutamic acid can be increased by deficiency of the pknG gene that controls the activity of ODHC which catalyzes the conversion of 2-oxoglutaric acid to succinyl-CoA in the TCA cycle.

Furthermore, *Brevibacillus choshinensis* has reduced extracellular proteolytic activity and is used as a high secretion production system of heterologous proteins. The extracellular proteolytic activity can be further reduced by deleting the emp gene encoding the extracellular protease.

In genetic modification in conventional methods, however, since the object gene is degraded by inserting a foreign gene by homologous recombination and deleting the genome gene, the obtained microorganism falls under a gene recombinant microorganism. To secure safety, therefore, the facility costs and waste disposal costs become large, and the production costs become problematically high.

In recent years, genome editing is attracting attention as a technique for modifying the object gene and genome region in various species. Conventionally, as a method of genome editing, a method utilizing an artificial nuclease comprising a molecule having a sequence-independent DNA cleavage ability and a molecule having a sequence recognition ability in combination has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1), a method of cleaving or modifying a target gene in a particular nucleotide sequence or a site adjacent thereto by using TALEN wherein a transcription activator-like (TAL) effector which is a DNA binding module that the plant pathogenic bacteria *Xanthomonas* has, and a DNA endonuclease are linked (patent document 2), a method utilizing CRISPR-Cas9 system wherein DNA sequence CRISPR (Clustered Regularly interspaced short palindromic repeats) that functions in an acquired immune system possessed by eubacterium and archaebacterium, and nuclease Cas (CRISPR-associated) protein family having an important function along with CRISPR are m combined (patent document 3) and the like have been reported. Furthermore, a method of cleaving a target gene in the vicinity of a particular sequence, by using artificial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

The genome editing techniques heretofore been proposed basically presuppose double-stranded DNA breaks (DSB) by nuclease. This is because the genome editing technique is based on an idea that a foreign gene may be more easily inserted into the desired region if a particular region in the genome can be cleaved, which stems from the finding that DSB promotes homologous recombination.

However, since DSB includes unexpected genome modifications, side effects such as strong cytotoxicity, chromosomal rearrangement and the like occur, and it has problems of extremely small number of surviving cells and difficulty in genetic modification itself in unicellular microorganisms.

DOCUMENT LIST

Patent Documents patent document 1: JP-B-4968498
patent document 2: National Publication of International Patent Application No. 2013-513389
patent document 3: National Publication of International Patent Application No. 2010-519929
patent document 4: JP-A-2013-128413

Non-Patent Document non-patent document 1: Kelvin M Esvelt, Harris H Wang (2013) Genome-scale engineering for systems and synthetic biology, Molecular Systems Biology 9: 641

SUMMARY OF THE INVENTION

Problems to be Solved by the Invention

An object of the present invention is to provide a novel method of genome editing for modifying a nucleic acid base of a particular sequence of a genome gene of gram-positive bacterium without DSB or insertion of foreign DNA fragment, i.e., by non-cleavage of a double stranded DNA or single strand cleavage, and without relying on the insertion of foreign DNA fragment or deletion of genome DNA fragment, and a complex of a nucleic acid sequence-recognizing module and a nucleic acid base converting enzyme therefor.

Means of Solving the Problems

The present inventors have conducted intensive studies in an attempt to solve the above-mentioned problems and took note of adopting base conversion by a conversion reaction of DNA base, without accompanying DSB and insertion and/or deletion of DNA fragment. The base conversion reaction by a deamination reaction of DNA base is already known; however, targeting any site by recognizing a particular sequence of DNA, and specifically modifying the targeted DNA by base conversion of DNA bases has not been realized yet.

Therefore, deaminase that catalyzes a deamination reaction was used as an enzyme for such conversion of nucleic acid bases, and a genome sequence was modified by nucleic acid base conversion in a region containing a particular DNA sequence of three kinds of gram-positive bacteria, by forming a complex of the enzyme and a molecule having a DNA sequence recognition ability (nucleic acid sequence-recognizing module).

To be specific, CRISPR-Cas system (CRISPR-mutant Cas) was used. That is, a DNA encoding a chimeric RNA molecule (guide RNA) wherein genome specific CRISPR-RNA:crRNA (gRNA) containing a sequence (targeting sequence) complementary to a target nucleotide sequence of a gene to be modified is linked to an RNA (trans-activating crRNA: tracrRNA) for recruiting Cas protein was produced, a DNA wherein a DNA encoding a mutant Cas protein (dCas) wherein cleavage ability of both strands of a double stranded DNA is inactivated and a deaminase gene are linked was produced, and these DNAs were introduced into gram-positive bacteria by using an expression vector functionable in each host cell. As a result, the desired base in the target nucleotide sequence could be successfully substituted by other base.

The present inventor have conducted further studies based on these findings and completed the present invention.

Accordingly, the present invention is as described below.
[1] A method of modifying a targeted site in a double stranded DNA of a gram-positive bacterium, comprising a step of contacting a complex wherein a nucleic acid sequence-recognizing module that specifically binds to a target nucleotide sequence in a given double stranded DNA and a nucleic acid base converting enzyme are bonded, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site, wherein the double stranded DNA is contacted with the complex by introducing the nucleic acid encoding the complex into the gram-positive bacterium.
[2] The method of the above-mentioned [1], wherein the aforementioned nucleic acid sequence-recognizing module is selected from the group consisting of a CRISPR-Cas system wherein at least one DNA cleavage ability of Cas is inactivated, a zinc finger motif, a TAL effector and a PPR motif.
[3] The method of the above-mentioned [1], wherein the aforementioned nucleic acid sequence-recognizing module is a CRISPR-Cas system wherein at least one DNA cleavage ability of Cas is inactivated.
[4] The method of any of the above-mentioned [1] to [3], which uses two or more kinds of nucleic acid sequence-recognizing modules respectively specifically binding to different target nucleotide sequences.
[5] The method of the above-mentioned [4], wherein the aforementioned different target nucleotide sequence is present in a different gene.
[6] The method of any of the above-mentioned [1] to [5], wherein the aforementioned nucleic acid base converting enzyme is deaminase.
[7] The method of the above-mentioned [6], wherein the aforementioned deaminase is cytidine deaminase.
[8] The method of any one of the above-mentioned [1] to [7], wherein the aforementioned gram-positive bacterium is a microorganism other than the genus *Bacillus*.
[9] The method of the above-mentioned [8], wherein the aforementioned gram-positive bacterium is a microorganism belonging to the genus *Clostridium*, the genus *Brevibacillus* or the genus *Corynebacterium*.
[10] The method of the above-mentioned [9], wherein the microorganism belonging to the genus *Clostridium* is *Clostridium saccharoperbutylacetonicum*.
[11] The method of the above-mentioned [9], wherein the microorganism belonging to the genus *Brevibacillus* is *Brevibacillus choshinensis*.
[12] The method of the above-mentioned [9], wherein the microorganism belonging to the genus *Corynebacterium* is *Corynebacterium glutamicum*.
[13] The method of any of the above-mentioned [1] to [12], comprising a step of introducing an expression vector comprising a nucleic acid encoding the aforementioned complex in a form permitting control of an expression period into the aforementioned gram-positive bacterium, and a step of inducing expression of the nucleic acid for a period necessary for fixing the modification of the targeted site in the double stranded DNA.
[14] A nucleic acid-modifying enzyme complex of a nucleic acid sequence-recognizing module that specifically binds to a target nucleotide sequence in a double stranded DNA of a gram-positive bacterium and a nucleic acid base converting enzyme bonded to each other, which complex converts one or more nucleotides in the targeted site to other one or more nucleotides or deletes one or more nucleotides, or inserts one or more nucleotides into said targeted site, without cleaving at least one strand of said double stranded DNA in the targeted site and is functionable in the gram-positive bacterium.
[15] A nucleic acid encoding the nucleic acid-modifying enzyme complex of the above-mentioned [14].

Effect of the Invention

According to the genome editing technique of the present invention, since it does not accompany insertion of a foreign DNA or double-stranded DNA breaks, the technique is superior in safety, and has no small possibility of affording a solution to cases causing biological or legal disputes on conventional methods as relating to gene recombination microorganism. For example, reduction of the facility costs and waste disposal cost can be expected in industrial fermentative production using gram-positive bacteria, and therefore, the technique is economically advantageous.

BRIEF DESCRIPTION OF THE DRAWINGS

The FIGURE schematically shows the structure of avector plasmid for disruption.

DESCRIPTION OF EMBODIMENTS

The present invention provides a method of modifying a targeted site of a double stranded DNA in gram-positive bacterium by converting the target nucleotide sequence and nucleotides in the vicinity thereof in the double stranded DNA to other nucleotides, without cleaving at least one strand of the double stranded DNA to be modified (hereinafter sometimes to be also referred to as "the method of the present invention"). The method characteristically contains a step of contacting a complex wherein a nucleic acid sequence-recognizing module that specifically binds to the target nucleotide sequence in the double stranded DNA and a nucleic acid base converting enzyme are bonded with the double stranded DNA in the host gram-positive bacterium to convert the targeted site, i.e., the target nucleotide sequence and nucleotides in the vicinity thereof, to other nucleotides, or the like.

The gram-positive bacterium usable for the method of the present invention is not particularly limited as long as it is positive to gram-staining and a vector replicatable in the bacterial cell thereof is available. It is preferably a useful bacterium utilized for traditional fermentative production and new biotechnology. For example, bacteria belonging to the genus *Clostridium*, genus *Bacillus*, genus *Streptomyces*, genus *Corynebacterium*, genus *Brevibacillus*, genus *Bifidobacterium*, genus *Lactococcus*, genus *Enterococcus*, genus *Pediococcus*, genus *Leuconostoc*, genus *Streptomyces* and the like, and the like can be mentioned. Preferably, it is a bacterium belonging to a genus other than the genus *Bacillus*. More preferably, bacteria belonging to the genus *Clostridium*, genus *Brevibacillus*, genus *Corynebacterium* can be mentioned. Examples of the bacterium belonging to the genus *Clostridium* include *Clostridium saccharoperbutylacetonicum* and the like, examples of the bacterium belonging to the genus *Brevibacillus* include *Brevibacillus choshinensis* and the like, and examples of the bacterium belonging to the genus *Corynebacterium* include *Corynebacterium glutamicum* and the like.

In the present invention, the "modification" of a double stranded DNA means that a nucleotide (e.g., dC) on a DNA strand is converted to other nucleotide (e.g., dT, dA or dG), or deleted, or a nucleotide or a nucleotide sequence is inserted between certain nucleotides on a DNA strand. While the double stranded DNA to be modified is not particularly limited as long as it is a double stranded DNA present in the host cell, it is preferably a genomic DNA. The "targeted site" of a double stranded DNA means the whole or partial "target nucleotide sequence", which a nucleic acid sequence-recognizing module specifically recognizes and binds to, or the vicinity of the target nucleotide sequence (one or both of 5' upstream and 3' downstream). In addition, the "target nucleotide sequence" means a sequence to which a nucleic acid sequence-recognizing module in the double stranded DNA binds.

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a nucleic acid base converting enzyme linked to the module to specifically act on a targeted site of a double stranded DNA.

In the present invention, the "nucleic acid base converting enzyme" means an enzyme capable of converting a target nucleotide to other nucleotide by catalyzing a reaction for converting a substituent on a purine or pyrimidine ring on a DNA base to other group or atom, without cleaving the DNA strand.

In the present invention, the "nucleic acid-modifying enzyme complex" means a molecular complex comprising a complex comprising the above-mentioned nucleic acid sequence-recognizing module and nucleic acid base converting enzyme are connected, and having nucleic acid base converting enzyme activity and imparted with a particular nucleotide sequence recognition ability. The "complex" here encompasses not only one constituted of multiple molecules, but also one having a nucleic acid sequence-recognizing module and a nucleic acid base converting enzyme in a single molecule, like a fusion protein.

The nucleic acid base converting enzyme to be used in the method of the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter to be also referred to as AID) which is an enzyme that introduces a mutation into an immunoglobulin gene in the acquired immunity of vertebrata or the like.

While the derivation of nucleic acid base converting enzyme is not particularly limited, in the case of cytidine deaminase, for example, PmCDA1 derived from *Petromyzon marinus* (*Petromyzon marinus* cytosine deaminase 1) or AID (Activation-induced cytidine deaminase; AICDA) derived from vertebrata (e.g., mammal such as human, swine, bovine, dog, chimpanzee and the like, birds such as chicken and the like, amphibian such as xenopus and the like, fish such as zebrafish, sweetfish, channel catfish and the like, and the like) can be used.

A target nucleotide sequence in a double stranded DNA to be recognized by the nucleic acid sequence-recognizing module in the nucleic acid-modifying enzyme complex of the present invention is not particularly limited as long as the module specifically binds to, and may be any sequence in the double stranded DNA. The length of the target nucleotide sequence only needs to be sufficient for specific binding of the nucleic acid sequence-recognizing module. It is, for example, not less than 12 nucleotides, preferably not less than 15 nucleotides, more preferably not less than 18 nucleotides, according to the genome size of gram-positive bacterium. While the upper limit of the length is not particularly limited, it is preferably not more than 25 nucleotides, more preferably not more than 22 nucleotides.

As the nucleic acid sequence-recognizing module in the nucleic acid-modifying enzyme complex of the present invention, CRISPR-Cas system wherein at least one DNA cleavage ability of Cas is inactivated (CRISPR-mutant Cas), zinc finger motif, TAL effector and PPR motif and the like, as well as a fragment containing a DNA binding domain of a protein that specifically binds to DNA, such as restriction enzyme, transcription factor, RNA polymerase and the like, and free of a DNA double strand cleavage ability and the like can be used, but the module is not limited thereto. Preferably, CRISPR-mutant Cas, zinc finger motif, TAL effector, PPR motif and the like can be mentioned.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. The above-mentioned patent document 2 can be referred to as for the detail of the production of TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(−2) amino acids of each motif. Motif constitution has no dependency, and is free of interference of motifs on both sides. Therefore, like TAL effector, a PPR protein specific to the target nucleotide sequence can be produced by simply connecting PPR motifs. The above-mentioned patent document 4 can be referred to as for the detail of the production of PPR motif.

When a fragment of restriction enzyme, transcription factor, RNA polymerase and the like is used, since the DNA binding domains of these proteins are well known, a fragment containing the domain and free of a DNA double strand cleavage ability can be easily designed and constructed.

Any of the above-mentioned nucleic acid sequence-recognizing module can be provided as a fusion protein with the above-mentioned nucleic acid base converting enzyme, or a protein binding domain such as SH3 domain, PDZ domain, GK domain, GB domain and the like and a binding partner thereof may be fused with a nucleic acid sequence-recognizing module and a nucleic acid base converting enzyme, respectively, and provided as a protein complex via an interaction of the domain and a binding partner thereof. Alternatively, a nucleic acid sequence-recognizing module and a nucleic acid base converting enzyme may be each fused with intein, and they can be linked by ligation after protein synthesis.

The nucleic acid-modifying enzyme complex of the present invention containing a complex (including fusion protein) wherein a nucleic acid sequence-recognizing module and a nucleic acid base converting enzyme are bonded may be contacted with a double stranded DNA by introducing a nucleic acid encoding the complex into gram-positive bacterium having the object double stranded DNA (e.g., genomic DNA).

Therefore, the nucleic acid sequence-recognizing module and the nucleic acid base converting enzyme are prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA. When it is a DNA, it is preferably a double stranded DNA, and provided in the form of an expression vector disposed under regulation of a functional promoter in a host cell. When it is an RNA, it is preferably a single strand RNA.

Since the complex of the present invention wherein a nucleic acid sequence-recognizing module and a nucleic acid base converting enzyme are bonded does not accompany double-stranded DNA breaks (DSB), genome editing with low toxicity is possible, and the genetic modification method of the present invention can be applied to a wide range of gram-positive bacteria in general.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding a nucleic acid base converting enzyme can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding PmCDA1 of *Petromyzon marinus* can be cloned by designing suitable primers for the upstream and downstream of CDS based on the cDNA sequence (accession No. EF094822) registered in the NCBI database, and cloning from *Petromyzon marinus*-derived mRNA by the RT-PCR method. A DNA encoding human AID can be cloned by designing suitable primers for the upstream and downstream of CDS based on the cDNA sequence (accession No. AB040431) registered in the NCBI database, and cloning from, for example, human lymph node-derived mRNA by the RT-PCR method. AID homologue derived from other vertebrata can also be cloned in the same manner as in the above and based on known cDNA sequence information (e.g., swine (accession No. CU582981), bovine (accession No. NM_110138682), dog (accession No. NM_001003380), chimpanzee (accession No. NM_001071809), chicken (accession No. NM_001243222), xenopus (accession No. NM_001095712), zebrafish (accession No. AAI62573), sweetfish (accession No. AB619797), channel catfish (accession No. NM_001200185) etc.).

The cloned DNA may be directly, or after digestion with a restriction enzyme when desired, or after addition of a suitable linker, ligated with a DNA encoding a nucleic acid sequence-recognizing module to prepare a DNA encoding a fusion protein. Alternatively, a DNA encoding a nucleic acid sequence-recognizing module, and a DNA encoding a nucleic acid base converting enzyme may be each fused with a DNA encoding a binding domain or a binding partner thereof, or both DNAs may be fused with a DNA encoding a separation intein, whereby the nucleic acid sequence-recognizing conversion module and the nucleic acid base converting enzyme are translated in a host cell to form a complex. In these cases, a linker can be linked to a suitable position of one of or both DNAs when desired.

A DNA encoding a nucleic acid sequence-recognizing module and a DNA encoding a nucleic acid base converting enzyme can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (www.kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency.

An expression vector containing a DNA encoding a nucleic acid sequence-recognizing module and/or a nucleic acid base converting enzyme can be produced, for example, by linking the DNA to the downstream of a promoter in a suitable expression vector.

For example, as a vector replicatable in the genus *Clostridium*, a shuttle vector of *Escherichia coli* and the genus *Clostridium* is convenient. For example, pKNT19 derived from pIM13 (Journal of General Microbiology, 138, 1371-1378 (1992)), pJIR756 and pNAK1 can be mentioned. In addition, as a vector replicatable in the genus *Brevibacillus*, pUB110 derived from *Brevibacillus brevis* can be mentioned and as a vector replicatable in the genus *Corynebacterium*, pCG100-pHSG398 hybrid plasmid derived from *Corynebacterium glutamicum* can be mentioned. Furthermore, as a vector replicatable in the genus *Lactobacillus*, pLAB1000 derived from *Lactobacillus* lactic and the like can be mentioned.

As the promoter, any promoter appropriate for a host to be used for gene expression can be used. In a conventional method using DSB, since the survival rate of the host cell sometimes decreases markedly due to the toxicity, it is desirable to increase the number of cells by the start of the induction by using an inductive promoter. However, since sufficient cell proliferation can also be afforded by expressing the nucleic acid-modifying enzyme complex of the present invention, a constitution promoter can also be used without limitation.

The expression vector can contained, when desired, a terminator, a repressor, a selection marker such as drug resistance gene, auxotrophic complementary gene and the like, replication origin functionable in *Escherichia coli* etc., and the like.

An RNA encoding a nucleic acid sequence-recognizing module and/or a nucleic acid base converting enzyme can be prepared by, for example, transcription to mRNA in a vitro transcription system known per se by using a vector encoding DNA encoding the above-mentioned nucleic acid sequence-recognizing module and/or a nucleic acid base converting enzyme as a template.

A complex of a nucleic acid sequence-recognizing module and a nucleic acid base converting enzyme can be intracellularly expressed by introducing an expression vector containing a DNA encoding a nucleic acid sequence-recognizing module and/or a nucleic acid base converting enzyme into a host cell, and culturing the host cell.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host.

A gram-positive bacterium introduced with a vector can be cultured according to a known method according to the kind thereof. A liquid medium is preferable as a medium to be used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5-about 8.

Gram-positive bacteria are cultured generally at about 30-about 40° C. Where necessary, aeration and stirring may also be performed.

As mentioned above, a complex of a nucleic acid sequence-recognizing module and a nucleic acid base converting enzyme, i.e., nucleic acid-modifying enzyme complex, can be expressed intracellularly.

An RNA encoding the nucleic acid sequence-recognizing module and/or nucleic acid base converting enzyme can be introduced into gram-positive bacterium by a method known per se. The introduction of RNA can be performed once or repeated multiple times (e.g., 2-5 times) at suitable intervals.

When a complex of a nucleic acid sequence-recognizing module and a nucleic acid base converting enzyme is expressed by an expression vector or RNA molecule introduced into the cell, the nucleic acid sequence-recognizing module specifically recognizes and binds to a target nucleotide sequence in the double stranded DNA (e.g., genomic DNA) of interest and, due to the action of the nucleic acid base converting enzyme linked to the nucleic acid sequence-recognizing module, base conversion occurs in the sense strand or antisense strand of the targeted site (whole or partial target nucleotide sequence or the vicinity thereof) and a mismatch occurs in the double stranded DNA (e.g., when cytidine deaminase such as PmCDA1, AID and the like is used as a nucleic acid base converting enzyme, cytosine on the sense strand or antisense strand at the targeted site is converted to uracil to cause U:G or G:U mismatch). When the mismatch is not correctly repaired, and when repaired such that a base of the opposite strand forms a pair with a base of the converted strand (T-A or A-T in the above-mentioned example), or when other nucleotide is further substituted (e.g., U→A, G) or when one to several dozen bases are deleted or inserted during repair, various mutations are introduced.

As for zinc finger motif, production of many actually functionable zinc finger motifs is not easy, since production efficiency of a zinc finger that specifically binds to a target nucleotide sequence is not high and selection of a zinc finger having high binding specificity is complicated. While TAL effector and PPR motif have a high degree of freedom of target nucleic acid sequence recognition as compared to zinc finger motif, a problem remains in the efficiency since a large protein needs to be designed and constructed every time according to the target nucleotide sequence.

In contrast, since the CRISPR-Cas system recognizes the object double stranded DNA sequence by a guide RNA complementary to the target nucleotide sequence, any sequence can be targeted by simply synthesizing an oligoDNA capable of specifically forming a hybrid with the target nucleotide sequence.

Therefore, in a more preferable embodiment of the present invention, a CRISPR-Cas system wherein at least one DNA cleavage ability of Cas is inactivated (CRISPR-mutant Cas), a zinc finger motif, a TAL effector and a PPR motif is used as a nucleic acid sequence-recognizing module.

The nucleic acid sequence-recognizing module of the present invention using CRISPR-mutant Cas is provided as a complex of a chimeric RNA (guide RNA) consisting of a CRISPR-RNA (crRNA) comprising a sequence complementary to the target nucleotide sequence and trans-activating RNA (tracrRNA) necessary for recruiting mutant Cas protein, and a mutant Cas protein.

While the Cas protein to be used in the present invention is not particularly limited as long as it forms a complex with guide RNA and can recognize and bind to the target nucleotide sequence in the object gene and a protospacer adjacent motif (PAM) adjacent thereto, it is preferably Cas9. Examples of Cas9 include, but are not limited to, Cas9 (SpCas9) derived from *Streptococcus pyogenes*; PAM sequence NGG (N is A, G, T or C, hereinafter the same)), Cas9 (StCas9; PAM sequence NNAGAAW) derived from *Streptococcus thermophilus*, Cas9 (MmCas9; PAM sequence NNNNGATT) derived from *Neisseria meningitidis* and the like. Preferred is SpCas9 with less restriction by PAM (substantially 2 bases, and can target theoretically any site on the genome). As a mutant Cas to be used in the present invention, any of Cas wherein the cleavage ability of the both strands of the double stranded DNA is inactivated and one having nickase activity wherein at least one cleavage ability of one strand alone is inactivated can be used. For example, in the case of SpCas9, a D10A mutant wherein the 10th Asp residue is converted to an Ala residue and lacking cleavage ability of a strand opposite to the strand forming a complementary strand with a guide RNA, or H840A mutant wherein the 840th His residue is converted to an Ala residue and lacking cleavage ability of strand complementary to guide RNA, or a double mutant thereof can be used, and other mutant Cas can be used similarly.

The nucleic acid base converting enzyme is provided as a complex with mutant Cas by a method similar to the coupling scheme with the above-mentioned zinc finger and the like. Alternatively, a nucleic acid base converting enzyme and mutant Cas can also be bound by utilizing RNA aptamers MS2F6, PP7 and the like and RNA scaffold by binding proteins thereto. The targeting sequence in the guide RNA forms a complementary strand with the target nucleotide sequence, mutant Cas is recruited by the tracrRNA attached and mutant Cas recognizes PAM. One or both DNAs cannot be cleaved and, due to the action of the nucleic acid base converting enzyme linked to the mutant Cas, base conversion occurs in the targeted site (appropriately adjusted within several hundred bases including whole or partial target nucleotide sequence) and a mismatch occurs in the double stranded DNA. When the mismatch is not correctly repaired, and when repaired such that a base of the opposite strand forms a pair with a base of the converted strand, or when other nucleotide is further converted or when one to several dozen bases are deleted or inserted during repair, various mutations are introduced.

Even when CRISPR-mutant Cas is used as a nucleic acid sequence-recognizing module, a nucleic acid sequence-recognizing module and a nucleic acid base converting enzyme are desirably introduced, in the form of a nucleic acid encoding same, into gram-positive bacterium having a double stranded DNA of interest, similar to when zinc finger and the like are used as a nucleic acid sequence-recognizing module.

A DNA encoding Cas can be cloned by a method similar to the above-mentioned method for a DNA encoding a nucleic acid base converting enzyme, from a cell producing the enzyme. A mutant Cas can be obtained by introducing a mutation to convert an amino acid residue of the part important for the DNA cleavage activity (e.g., 10th Asp residue and 840th His residue for Cas9, though not limited thereto) to other amino acid, into a DNA encoding cloned Cas, by a site specific mutation induction method known per se.

Alternatively, a DNA encoding mutant Cas can also be constructed as a DNA showing codon usage suitable for expression in a host cell to be used, by a method similar to to those mentioned above for a DNA encoding a nucleic acid sequence-recognizing module and a DNA encoding a nucleic acid base converting enzyme, and by a combination of chemical synthesis or PCR method or Gibson Assembly method.

A DNA encoding a mutant Cas and a DNA encoding a nucleic acid base converting enzyme may be linked to allow for expression as a fusion protein, or designed to be separately expressed using a binding domain, intein and the like, and form a complex in a host cell via protein-protein interaction and protein ligation.

The obtained DNA encoding a mutant Cas and/or a nucleic acid base converting enzyme can be inserted into the downstream of a promoter of an expression vector similar to the one mentioned above, according to the host.

On the other hand, a DNA encoding a guide RNA can be chemically synthesized by designing an oligoDNA sequence in which a crRNA sequence containing a nucleotide sequence (also referred to as "targeting sequence") complementary to a "targeted strand" of the target nucleotide sequence, and a known tracrRNA sequence (e.g., gttttagagctagaaatagcaagttaaaataaggctagtccgttatcaacttgaaaaagtggc accgagtcggtggtgctttt; SEQ ID NO: 1) are linked, and using a DNA/RNA synthesizer.

The "targeted strand" here means a strand forming a hybrid with crRNA of the target nucleotide sequence, and an opposite strand thereof that becomes single-stranded by hybridization to the targeted strand and crRNA is referred to as a "non-targeted strand". Since the nucleic acid base conversion reaction is generally assumed to frequently occur on a single stranded non-targeted strand, when the target nucleotide sequence is to be expressed by one of the strands (e.g., when PAM sequence is indicated, when positional relationship of target nucleotide sequence and PAM is shown etc.), it is represented by a sequence of the non-targeted strand.

While the length of the targeting sequence is not particularly limited as long as it can specifically bind to a target nucleotide sequence, for example, it is 15-30 nucleotides, preferably 18-25 nucleotides. The selection of the target nucleotide sequence is restricted by the presence of an adjacent PAM on the 3'-side of the sequence. According to the system of the present invention in which CRISPR-mutated Cas and cytidine deaminase are combined, mutation is easily introduced into C at a position within 7 nucleotides from the 5'-end thereof irrespective of the length of the target nucleotide sequence. Therefore, by appropriately determining the length of the target nucleotide sequence (targeting sequence as a complementary strand thereof), the site of a base into which a mutation can be introduced can be shifted. As a result, restriction by PAM (NGG in SpCas9) can be removed at least partially, and the degree of freedom of mutation introduction becomes higher.

A targeting sequence can be designed, for example, using a guide RNA design website open to public (CRISPR Design Tool, CRISPRdirect etc.) by listing up 20 mer sequences having PAM (e.g., NGG) adjacent to the 3'-side from the CDS sequences of the object gene, and selecting a sequence that causes an amino acid change in the protein encoded by the target gene when C within 7 nucleotides from the 5' end is converted to T. Furthermore, a sequence having C that similarly causes, when the length of the targeting sequence is changed, for example, within the range of 18-25 nucleotides, an amino acid change by base conversion to T within 7 nucleotides from the 5' end thereof is selected. A candidate sequence having a small number of off-target sites in the object gram-positive bacterial genome can be used as a targeting sequence. CRISPR Design Tool and CRISPRdirect currently do not have a function to search off-target sites of gram-positive bacteria. Off-target sites can be searched by applying a Blast search to the genome of the gram-positive bacterium serving as a host, for example, 8-12 nucleotides on the 3'-side of the candidate sequence (seed sequence with high discrimination ability of target nucleotide sequence).

While a DNA encoding guide RNA can also be inserted into an expression vector similar to the one mentioned above, according to the host. As the promoter, pol III system promoter (e.g., SNR6, SNR52, SCR1, RPR1, U6, H1 promoter etc.) and terminator (e.g., $T_6$ sequence) are preferably used. When a pol III system promoter is used, a nucleotide sequence having four or more consecutive T's should not be selected as a targeting sequence.

An RNA encoding mutant Cas and/or a nucleic acid base converting enzyme can be prepared by, for example, transcription to mRNA in a vitro transcription system known per se by using a vector encoding the above-mentioned mutant Cas and/or DNA encoding a nucleic acid base converting enzyme as a template.

Guide RNA (crRNA-tracrRNA) can be obtained by designing an oligoDNA sequence linking a sequence complementary to the targeted strand of the target nucleotide sequence and known tracrRNA sequence and chemically synthesizing using a DNA/RNA synthesizer.

A DNA or RNA encoding mutant Cas and/or a nucleic acid base converting enzyme, guide RNA (crRNA-tracr-RNA) or a DNA encoding same can be introduced into a gram-positive bacterium by a method similar to the above, according to the host.

Since conventional artificial nuclease accompanies Double-stranded DNA breaks (DSB), inhibition of growth and cell death assumedly caused by disordered cleavage of chromosome (off-target cleavage) occur by targeting a sequence in the genome. The effect thereof is particularly fatal for many microorganisms and prokaryotes, and prevents applicability. In the present invention, mutation is introduced not by DNA cleavage but by a conversion reaction of the substituent on the DNA base (particularly deamination reaction), and therefore, drastic reduction of toxicity can be realized.

The modification of the double stranded DNA in the present invention does not prevent occurrence of cleavage of the double stranded DNA in a site other than the targeted site (appropriately adjusted within several hundred bases including whole or partial target nucleotide sequence). However, one of the greatest advantages of the present invention is avoidance of toxicity by off-target cleavage, which is generally applicable to any species. In preferable one embodiment, therefore, the modification of the double stranded DNA in the present invention does not accompany cleavage of DNA strand not only in a targeted site of a given double stranded DNA but in a site other than same.

In the below-mentioned Examples, double mutant Cas9 is used, and the present inventors found that when other microorganism such as budding yeast, Escherichia coli and the like is used as a host and Cas having a nickase activity capable of cleaving only one of the strands of the double stranded DNA is used as a mutant Cas, the mutation introduction efficiency increases as compared to mutant Cas incapable of cleaving both strands. Therefore, for example, when a protein having a nickase activity is further linked in addition to a nucleic acid sequence-recognizing module and a nucleic acid base converting enzyme and only a DNA single strand is cleaved in the vicinity of the target nucleotide sequence, the mutation introduction efficiency can be improved while avoiding the strong toxicity of DSB. Furthermore, a comparison of the effects of mutant Cas having two kinds of nickase activity of cleaving different strand confirmed mutated sites gathering near the center of the target nucleotide sequence in one of them and various mutations randomly introduced into region of several hundred bases from the target nucleotide sequence in the other. Therefore, also in the present invention, by selecting a strand to be cleaved by the nickase, a mutation can be introduced into a particular nucleotide or nucleotide region of the double stranded DNA of gram-positive bacterium at a pinpoint, or various mutations can be randomly introduced into a comparatively wide range, which can be property adopted according to the object.

The present inventors also confirmed using a budding yeast that when sequence-recognizing modules are produced corresponding to the adjacent multiple target nucleotide sequences, and simultaneously used, the mutation introduction efficiency drastically increases than using a single nucleotide sequence as a target. As the effect thereof, similarly mutation induction is realized even when both target nucleotide sequences partly overlap or when the both are apart by about 600 bp. It can occur both when the target nucleotide sequences are in the same direction (targeted strand is the same strand), and when they are opposed (both strands of double stranded DNA are targeted strands).

The present inventors also confirmed using a budding yeast that the genome sequence modification method of the present invention can introduce mutation into almost all cells in which the nucleic acid-modifying enzyme complex of the present invention has been expressed, by selecting a suitable target nucleotide sequence. Thus, insertion and selection of a selection marker gene, which are essential in the conventional genome editing, are not necessary. This dramatically facilitates and simplifies gene manipulation and enlarges the applicability to molecule breeding of useful microorganism and the like since a recombinant microorganism with foreign DNA is not produced.

Since the genome sequence modification method of the present invention shows extremely high mutation introduction efficiency, and does not require selection by markers, modification of multiple DNA regions at completely different positions as targets can be performed. Therefore, in one preferable embodiment of the present invention, two or more kinds of nucleic acid sequence-recognizing modules that specifically bind to different target nucleotide sequences (which may be present in one object gene, or two or more different object genes) can be used. In this case, each one of these nucleic acid sequence-recognizing modules and nucleic acid base converting enzyme form a nucleic acid-modifying enzyme complex. Here, a common nucleic acid base converting enzyme can be used. For example, when CRISPR-Cas system is used as a nucleic acid sequence-recognizing module, a common complex (including fusion protein) of a Cas protein and a nucleic acid base converting enzyme is used, and two or more kinds of chimeric RNAs of tracrRNA and each of two or more crRNAs that respectively form a complementary strand with a different target nucleotide sequence are produced and used as guide RNA (crRNA-tracrRNA). On the other hand, when zinc finger motif, TAL effector and the like are used as nucleic acid sequence-recognizing modules, for example, a nucleic acid base converting enzyme can be fused with a nucleic acid sequence-recognizing module that specifically binds to a different target nucleotide.

To express the nucleic acid-modifying enzyme complex of the present invention in a host cell, as mentioned above, an expression vector containing a DNA encoding the nucleic acid-modifying enzyme complex, or an RNA encoding the nucleic acid-modifying enzyme complex is introduced into gram-positive bacterium. For efficient introduction of mutation, it is desirable to maintain an expression of nucleic acid-modifying enzyme complex of a given level or above for not less than a given period. From such aspect, it is ensuring to introduce an expression vector (plasmid etc.) autonomously replicatable in a host cell. However, since the plasmid etc. are foreign DNAs, they are preferably removed rapidly after successful introduction of mutation. Alternatively, when multiple target genes are to be successively modified and when usable one or more plasmids are incompatible, the previously introduced plasmid needs to be removed before introduction of the plasmid at a later stage. Therefore, though subject to change depending on the kind of host cell and the like, for example, the introduced plasmid is desirably removed from the host cell after a lapse of 6 hr-2 days from the introduction of an expression vector by using various plasmid removal methods well known in the art.

Alternatively, as long as expression of a nucleic acid modifying enzyme complex, which is sufficient for the introduction of mutation, is obtained, it is preferable to introduce mutation into the object double stranded DNA by transient expression by using an expression vector without autonomous replicatability in a host cell (e.g., vector etc. lacking replication origin that functions in host cell and/or gene encoding protein necessary for replication) or RNA.

Expression of target gene is suppressed while the nucleic acid-modifying enzyme complex of the present invention is expressed in gram-positive bacterium to perform a nucleic acid base conversion reaction. Therefore, it was difficult to directly edit a gene essential for the survival of the host cell as a target gene (due to side effects such as growth inhibition of host, unstable mutation introduction efficiency, mutation of site different from target and the like). In the present invention, direct editing of an essential gene can be realized efficiently by causing a nucleic acid base conversion reaction in a desired stage, and transiently expressing the nucleic acid-modifying enzyme complex of the present invention in a host cell for a period necessary for fixing the modification of the targeted site. While a period necessary for a nucleic acid base conversion reaction and fixing the modification of the targeted site varies depending on the kind of the host cell, culture conditions and the like, 2-20 generations are generally considered to be necessary. Those of ordinary skill in the art can appropriately determine a preferable expression induction period based on the doubling time of the host cell under culture conditions to be used. The expression induction period of the a nucleic acid encoding the nucleic acid-modifying enzyme complex of the present invention may be extended beyond the above-mentioned "period necessary for fixing the modification of the targeted site" as long as the host cell is free of side effects.

As a means for transiently expressing the nucleic acid-modifying enzyme complex of the present invention at a desired stage for a desired period, a method including producing a construct (expression vector) containing a nucleic acid (a DNA encoding a guide RNA and a DNA encoding a mutant Cas and nucleic acid base converting enzyme in the CRISPR-Cas system) encoding the nucleic acid-modifying enzyme complex, in a form capable of controlling the expression period, introducing the construct into gram-positive bacterium can be mentioned. The "form capable of controlling the expression period" is specifically, for example, a nucleic acid encoding the nucleic acid-modifying enzyme complex of the present invention placed under regulation of an inducible regulatory region. While the "inducible regulatory region" is not particularly limited, it is, for example, an operon of a temperature sensitive (ts) mutation repressor and an operator regulated thereby. Examples of the ts mutation repressor include, but are not limited to, ts mutation of λphage-derived cI repressor. In the case of λphage cI repressor (ts), it is bound to an operator to suppress expression of gene in the downstream at not more than 30° C. (e.g., 28° C.). At a high temperature of not less than 37° C. (e.g., 42° C.), it is dissociated from the operator to allow for induction of gene expression. Therefore, the period when the expression of the target gene is suppressed can be minimized by culturing a host cell introduced with a nucleic acid encoding nucleic acid-modifying enzyme complex generally at not more than 30° C., raising the temperature to not less than 37° C. at an appropriate stage, performing culture for a given period to carry out a nucleic acid base conversion reaction and, after introduction of mutation into the target gene, rapidly lowering the temperature to not more than 30° C. Thus, even when an essential gene for the host cell is targeted, it can be efficiently edited while suppressing the side effects.

When temperature sensitive mutation is utilized, for example, a temperature sensitive mutant of a protein necessary for autonomous replication of a vector is mounted on a vector containing a DNA encoding the nucleic acid-modifying enzyme complex of the present invention. As a result, autonomous replication cannot occur rapidly after expression of the nucleic acid-modifying enzyme complex, and the vector naturally falls off along with the cell division. Therefore, a combined use with cI repressor (ts) of the above-mentioned λphage simultaneously enables transient expression of the nucleic acid-modifying enzyme complex of the present invention, and removal of the plasmid.

The present invention is explained in the following by referring to Examples, which are not to be construed as limitative.

EXAMPLES

Example 1 Genetic Modification of *Clostridium saccharoperbutylacetonicum*

(1) Construction of Vector Plasmid for Disruption-Introduction of Modification CRISPR into pKNT19

A vector plasmid for disruption was constructed by inserting the following necessary gene sequence between the cleavage sites of the restriction enzymes BamHI and KpnI of plasmid pKNT19 replicatable in *Escherichia coli* and microorganisms of the genus *Clostridium*.

Amino acid mutation of D10A and H840A was introduced into *Streptococcus pyogenes* Cas9 gene containing bidirectional promoter region to give dCas9, and a construct to be expressed as a fusion protein with PmCDA1 was constructed via a linker sequence and, additionally, chimeric gRNA encoding a sequence (targeting sequence) complementary to the target nucleotide sequence of pta genes (SEQ ID NOs: 2 and 3) of *C. saccharoperbutylacetonicum* was mounted together therewith on a plasmid (full-length nucleotide sequence is shown in SEQ ID NO: 4 and each targeting sequence is inserted into the site of n20 (nucleotide Nos. 5560-5579) in the sequence) (see FIGURE).

(2) Introduction of Vector Plasmid for Disruption into *C. saccharoperbutylacetonicum*

Of the vector plasmids for disruption produced in the above-mentioned (1), 11757 or 1269+AatII was used to transform *C. saccharoperbutylacetonicum* ATCC27021 strain and ATCC27021Δptb1 strain (see Example 1 of JP-A-2014-207885). The targeting sequences and the like of the vector plasmid for disruption 11757, 1269+AatII are shown in Table 1.

TABLE 1

Outline of vector plasmids for disruption 11757, 1269+AatII

| vector for disruption | targeting sequence [a] (bold underline shows introduction site of mutation) | position of target nucleotide sequence in pta gene | main position of mutation introduction |
|---|---|---|---|
| 11757 | ctcttgataaatcatttat (5) | 916-934 of pta[b] | 932G > A, 934G > A |
| 1269+AatII | gctgcccatattttttcata (6) | 9-29 of pta | 24G > A, 25G > A |

[a] number in parenthesis shows SEQ ID NO.
[b] see SEQ ID NO: 2 for nucleotide sequence of pta gene Method As a preculture, a glycerol stock (0.5 mL) of *C. saccharoperbutylacetonicum* ATCC 27021 strain or ATCC 27021Δptb1 strain was inoculated to TYA medium (5 mL), and the cells were cultured at 30° C. for 24 hr. The composition of the TYA medium is shown in Table 2.

TABLE 2

| TYA medium composition | |
|---|---|
| glucose | 40 g |
| yeast extract | 2 g |
| tryptone•peptone | 6 g |
| $CH_3COONH_4$ | 3 g |
| $KH_2PO_4$ | 0.5 g |
| $MgSO_4•7H_2O$ | 0.3 g |
| $FeSO_4•7H_2O$ | 0.01 g |
| distilled water | 1 L |

The preculture medium was inoculated to TYA medium (10 mL) at OD=0.1 and incubated in a 15 mL-falcon tube at 37° C. At OD=0.6, the fermentation solution was centrifuged, the supernatant was removed, ice-cooled 65 mM MOPS buffer (pH 6.5) (10 mL) was added, and the mixture was resuspended by pipetting and centrifuged. Washing with MOPS buffer was repeated twice. MOPS buffer was removed by centrifugation and bacteria pellets were resuspended in ice-cooled 0.3 M sucrose (100 μL) to give a competent cell. The competent cell (50 μL) was charged in an Eppendorf tube and mixed with the plasmid (1 μg). It was placed in an ice-cooled cell for electroporation and the cell was impressed at Exponential dcay mode, 2.5 kV/cm, 25 pF, 350Ω. The electroporation apparatus used was Gene pulser xcell (Bio-rad). Thereafter, the total amount was inoculated to 5 mL of TYA medium and recovery cultured at 30° C. for about 2 hr. Thereafter, the recovered culture medium was applied on an MASS solid medium containing erythromycin (10 ppm), cultured at 30° C. for several days, culture was selected from the emerged colonies, and an erythromycin resistant strain introduced with the plasmid was obtained. Then, it was confirmed that the plasmid was maintained in the obtained strain. Four colonies each were inoculated in a TYA medium containing erythromycin (10 ppm), a region peculiar to the plasmid was amplified by PCR using a culture medium derived from the grown transformant colony as the template, the amplified product was analyzed by electrophoresis, and the presence or absence of plasmid retention was confirmed.

Results

All amplified products of the region peculiar to the plasmid were obtained. Therefore, it was clarified that a vector plasmid for disruption was maintained in the butanol fermentation bacteria.

(3) *C. saccharoperbutylacetonicum* Pta Gene Sequence Conversion Using Vector Plasmid for Disruption Using the vector plasmid for disruption, the DNA sequence of the pta gene of butanol fermentation bacteria was converted. Since vector plasmid for disruption does not have a control mechanism in the destructive tool, it functions by simply forming generations.

Method

The 11757/ATCC 27021Δptb1 strain as a 11757-carrying strain, 1269+AatII/ATCC 27021Δptb1 and 1269+AatII/ATCC 27021 strains as 1269+AatII-carrying strain, produced in the above-mentioned (2), were inoculated and cultured in TYA medium containing erythromycin (10 ppm), and dilution applied to TYA solid medium containing erythromycin (10 ppm) to give a single colony. The single colonies (8 colonies) were picked from 11757/ATCC 27021Δptb1 strain and 1269+AatII/ATCC 27021 strain and 16 colonies were taken from 1269+AatII/ATCC 27021Δptb1 and, using them as the templates, the full-length pta gene on the genome was amplified.

PCR Composition (in One Sample)
2×KODFX buffer 25 μL
2 mM dNTPS 10 μL
20 μM F primer 0.75 μL (NS-150414-i02)
20 μM R primer 0.75 μL (NS-150304-i04)
D.W. 11.5 μL
KODFX 1 μL sequence of NS-150414-i02
(SEQ ID NO: 7)
5'-GCCCTTTATGAAAGGGATTATATTCAG-3' sequence of NS-150304-i04
(SEQ ID NO: 8)
5'-GCTTGTACAGCAGTTAATGCAAC-3'

3.2 pmol primer 1 μL
Template DNA 0.35 μL
D.W. 14.15 μL

Template DNA and the primer were combined as follows.
1269+AatII-carrying strain
F side NS-150414-i02/R side NS-150304-i04
11753-carrying strain
F side NS-150525-i01/R side NS-150304-i04 sequence of NS-150525-i01
(SEQ ID NO: 9)
5'-GGTGTTACAGGAAATGTTGCAG-3'

PCR of the above-mentioned composition was performed under the following conditions.
96° C. 1 min
96° C. 10 sec→50° C. 5 sec→60° C. 4 min×25 cycles
10° C. hold After completion of the reaction, the sequence of the reaction product was analyzed by a DNA sequencer ABI PRISM3101.

Results

In the sequence analysis results of a colony derived from 11757/ATCC27021Δptb1, the 916-935th DNA sequence of the pta gene is shown in Table 3.

TABLE 3 sequence analysis results of colony derived from 11757/ATCC27021Δptb1

| sample | sequence [a]<br>bold underline shows<br>Introduction site of<br>mutation | position of mutation | | |
|---|---|---|---|---|
| original sequence | ataaatgatttatcaagagg (10) | — | — | — |
| #1 | ataaatgatttatcaaaagg (11) | c.932G > A | — | — |
| #2 | ataaatgatttatcaaaagg (11) | c.932G > A | — | — |
| #3 | ataaatgatttatcaagaag (12) | — | c.934G > A | — |
| #4 | ataaatgatttatcaaaagg (11) | c.932G > A | — | — |
| #5 | ataaatgatttatcaaaagg (11) | c.932G > A | — | — |
| #6 | ataaatgatttatcaaaaa (13) | c.932G > A | c.934G > A | c.935G > A |
| #7 | ataaatgatttatcaaaagg (11) | c.932G > A | — | — |
| #8 | ataaatgatttatcaaaagg (11) | c.932G > A | — | — |

[a] number in parenthesis shows SEQ ID NO.

49 μL each was dispensed, a single colony suspension (1 μL) was added as the template, and PCR was performed under the following conditions.
94° C. 2 min
98° C. 10 sec→50° C. 30 sec→68° C. 2 min×30 cycles
10° C. hold Then, the PCR product was purified by Wizard (registered trade mark) SV Gel and PCR Clean-Up System, and a sequence reaction was performed using the purified product as the template.
sequence reaction composition (for one sample)
Terminator Ready Reaction Mix 1 μL
5×Sequencing buffer 3.5 μL As a result, some mutation was introduced into all 8 strain whose sequences could be analyzed. From these results, it was confirmed that vector plasmid 11757 functions as a destructive tool plasmid for *Clostridium saccharoperbutylacetonicum*. As the position of mutation introduction, 6 strains were c.932G>A (932nd base G of pta gene was modified to A) mutation strains, 1 strain was c.934G>A, and 1 strain was c.932G>A, c.934G>A and c.935G>A mutation strain. By the mutation introduction of c.932G>A, the 311th amino acid arginine (encoded by AGA) of the PTA protein becomes lysine (encoded by AAA) and similarly becomes G312K by the mutation of c.934G>A and c.935G>A. Particularly, R311 is assumed to be activity center of PTA, and a drastic decrease in the enzyme activity by the mutation of c.932G>A was expected.

In the sequence analysis results of the colonies derived from 1269+AatII/ATCC27021 and 1269+AatII/ATCC27021Δptb1, the results of the 6-30th DNA sequence of the pta gene are respectively shown in Tables 4 and 5.

TABLE 4 sequence analysis results of colony derived from 1269+AatII/ATCc27021

| sample | sequence [a] bold underline shows introduction site of mutation | position of mutation | |
|---|---|---|---|
| original sequence | ccttatgaaaaaaatatgggcagca (14) | | |
| #1 | caaaaaaaaaaaaatatggacaaca (15) | c.25G > A | c.28G > A |
| #2 | ctataaaaaaaaatctttagataa (14) | - | - |
| #3 | ccttatgaaaaaaatatgaacagca (16) | c.24G > A | c.25G > A |
| #4 | ccttatgaaaaaaatatggacaaca (15) | c.25G > A | c.28G > A |
| #5 | ccttatgaaaaaaatatggacagca (17) | c.25G > A | |
| #6 | ccttatgaaaaaaatatggacagca (17) | c.25G > A | |
| #7 | ccttatgaaaaaaatatggacaaca (15) | c.25G > A | c.28G > A |
| #8 | ccttatgaaaaaaatatggacaaca (15) | c.25G > A | c.28G > A |

[a] number in parenthesis shows SEQ ID NO.

TABLE 5 sequence analysis results of colony derived from 1269+AatII/ATCC27021Δptb1

| sample | sequence [a] bold underline shows introduction site of mutation | position of mutation | |
|---|---|---|---|
| original sequence | ccttatgaaaaaaatatgggcagca (14) | | |
| #1 | ccttatgaaaaaaatatggacaaca (15) | c.25G > A | c.28G > A |
| #2 | ccttatgaaaaaaatatggacagca (17) | c.25G > A | |
| #3 | ccttatgaaaaaaatatggacagca (17) | c.25G > A | |
| #4 | ccttatgaaaaaaatatgaacagca (16) | c.24G > A | c.25G > A |
| #5 | ccttatgaaaaaaatatggacagca (17) | c.25G > A | |
| #6 | ccttatgaaaaaaatatggacagca (17) | c.25G > A | |
| #7 | ccttatgaaaaaaatatggacagca (17) | c.25G > A | |
| #8 | ccttatgaaaaaaatatggacagca (17) | c.25G > A | |
| #9 | ccttatgaaaaaaatatggacagca (17) | c.25G > A | |
| #10 | analysis not possible | | |
| #11 | ccttatgaaaaaaatatggacaaca (15) | c.25G > A | c.28G > A |
| #12 | analysis not possible | | |
| #13 | ccttatgaaaaaaatatggacagca (17) | c.25G > A | |
| #14 | ccttatgaaaaaaatatggacagca (17) | c.25G > A | |

TABLE 5-continued sequence analysis results of colony derived from
1269+AatII/ATCC27021Δptb1

| sample | sequence [a] bold underline shows introduction site of mutation | position of mutation | |
|---|---|---|---|
| #15 | ccttatgaaaaaaatatggacaaca (15) | c.25G > A | c.28G > A |
| #16 | ccttatgaaaaaaatatggacaaca (15) | c.25G > A | c.28G > A |

[a] number in parenthesis shows SEQ ID NO.

Some mutation was introduced into all 21 strains out of 22 strains whose sequences could be analyzed. From these results, it was confirmed that 1269+AatII functions as a destructive tool plasmid for *Clostridium saccharoperbutylacetonicum*. As the position of mutation introduction, the 25th G of the pta gene was changed to A in all strains with mutation introduction, and multiple strains had mutation of c.24G>A or c.28G>A. By the mutation introduction of c.24G>A, the 8th amino acid tryptophan (encoded by UGG) of the PTA protein changed to a stop codon (encoded by UGA), and the function is expected to be lost here since the protein synthesis is discontinued.

Example 2 Genetic Modification of *Corynebacterium glutamicum*

(1) Production of Shuttle Vector

A pCG100 plasmid derived from *C. glutamicum* ATCC13058 strain was obtained according to the method described in Example 1 of WO 2007/013695.

For ligation with pHSG398, pCG100 was digested with restriction enzyme BglII, and pHSG398 was digested with BamHI and dephosphorylated to prevent self ligation. pCG100 (digested with BglII) and pHSG398 (digested with BamHI) were ligated and introduced into *Escherichia coli*.

(2) Production of pknG Gene Modification Plasmid

PstI site was added to the both terminals of the DNA fragment (about 6 kbp HindIII-XhoI fragment of SEQ ID NO: 18) of modification CRISPR and inserted into the pCG100-pHSG398 plasmid at the site of cleavage with PstI to produce a modification CRISPR plasmid that functions in *C. glutamicum*. The targeting sequences (Table 6) for modification of the pknG gene (SEQ ID NO: 19 and 20) of *C. glutamicum* were designed, and Nos. 6, 7, 8 and 10 therefrom were inserted into the targeting sequence insertion site ($n_{20}$) (8773-8492nd nucleotides of SEQ ID NO: 18) of the modification CRISPR plasmid to give pknG gene modification plasmids.

TABLE 6

| No. | 20 base targeting sequence [a] | change on genome c (bold, underlined) changes to t [a] | base change | amino acid change |
|---|---|---|---|---|
| 1 | gcgagccacccaaggtcaaa (21) | gcgagccacccaaggtcaaa tgg (22) | c196t | R66X |
| 2 | cacccaaggtcaaatggtgg (23) | cacccaaggtcaaatggtgg tgg (24) | c205t | Q69X |
| 3 | caatcccgcccagttgctga (25) | caatcccgcccagttgctga tgg (26) | c376t | Q126X |
| 4 | caatcttccgttcaagacca (27) | caatcttccgttcaagacca agg (28) | c628t | Q210X |
| 5 | caagttaaactcatcgacct (29) | caagttaaactcatcgacct cgg (30) | c937t | Q313X |
| 6 | caatcaatcgagatccccct (31) | caatcaatcgagatccccct cgg (32) | c1561t | Q521X |
| 7 | gtccgagccctccttgacct (33) | gtccgagccctccttgacct agg (34) | c1591t | R531X |
| 8 | ccaatggctcgaaaccctag (35) | ccaatggctcgaaaccctag agg (36) | c1630t | Q544X |
| 9 | caatggctcgaaaccctaga (37) | caatggctcgaaaccctaga ggg (38) | c1630t | Q544X |
| 10 | tggcgacacaaatggttctc (39) | tggcgacacaaatggttctc cgg (40) | c1672t | R558X |

X: termination codon
[a] number in parenthesis shows SEQ ID NO.

(3) Introduction of pknG Gene Modification Plasmid into *C. glutamicum* and Confirmation of Genetic Modification The pknG gene modification plasmid produced in (2) was introduced into *C. glutamicum* ATCC 13032 strain according to the method described in Example 2 of WO 2007/013695. After transformation, colonies were formed in LBCm 60 ppm agar medium. The colonies were inoculated into LBCm 60 ppm liquid medium and subcultured twice, diluted and colonies were formed in the LB agar medium.

The colonies grown were cultured in the LB medium, pknG gene segments were amplified by PCR using the following primers, and the sequences thereof were analyzed. As a result, it could be confirmed that a stop codon was introduced into the assumed sites.

PCR primer F (SEQ ID NO: 41)

atgaaggataatgaagatttcgatccagattcac

PCR primer R (SEQ ID NO: 42)

gaaccaactcagtggccgc (4) Introduction of Other pknG Gene Modification Plasmid into *C. Glutamicum* and Confirmation of Genetic Modification In addition, the other targeting sequences described in Table 6 were inserted into a targeting sequence insertion site of the modification CRISPR plasmid of the above-mentioned (2) to give a pknG gene modification plasmid, and *C. glutamicum* ATCC 13032 strain was transformed by a method similar to that in the above-mentioned (3) to form a colony.

The colonies grown were cultured in the LB medium, pknG gene segments were amplified by PCR using the following primers, and the sequences thereof were analyzed. When the targeting sequence of No. 2 was used, a strain in which the 203rd C was changed to T and the encoding amino acid was changed from threonine to isoleucine, even though it was not formation of a stop codon, could be obtained.

PCR primer F (SEQ ID NO: 72)

cagcaaccgaagctgttgcc

PCR primer R (SEQ ID NO: 73)

gccatcagcaactgggcg

Example 3 Genetic Modification of *Brevibacillus choshinensis*

(1) Production of emp Gene Modification Plasmid

A pBIC1 plasmid usable in *B. choshinensis* was cleaved with restriction enzymes XhoI and HindIII, between which cleavage sites a necessary DNA fragment (about 6 kbp HindIII-XhoI fragment of the aforementioned SEQ ID NO: 18) of modification CRISPR was inserted to transform *B. choshinensis* to give a functionable modification CRISPR plasmid. The targeting sequences (Table 7) for modification of the emp gene (SEQ ID NO: 43 and 44) of *B. choshinensis* were designed, and Nos. 5, 6 and 7 therefrom were inserted into the targeting sequence insertion site ($n_{20}$) (8773-8792nd nucleotides of SEQ ID NO: 18) of the modification CRISPR plasmid to give emp gene modification plasmid.

TABLE 7

| No. | 20 base targeting sequence [a] | change on genome c (bold, underlined) changes to t [a] | base change | amino acid change |
|---|---|---|---|---|
| 1 | agcaagtgcgcgcttccaag (45) | gatgaca agcaagtgcgcgcttccaag cgg (46) | C364T | R122X |
| 2 | gcaagtgcgcgcttccaagc (47) | atgacaa gcaagtgcgcgcttccaagc ggg (48) | C364T | R122X |
| 3 | acaaagcgattccttgtgga (49) | tgccaaa acaaagcgattccttgtgga cgg (50) | C454T | Q152X |
| 4 | cagcctgaagatggcgcacc (51) | catgatt cagcctgaagatggcgcacc cgg (52) | C958T | Q320X |
| 5 | aagcaggcttcgctctacga (53) | acggaaa aagcaggcttcgctctacga tgg (54) | C1228T | Q410X |
| 6 | gcaagtagagaagacaccgc (55) | atatgcc gcaagtagagaagacaccgc cgg (56) | C1294T | Q432X |
| 7 | gaccagaagtttgatctgga (57) | agaaggc gaccagaagtttgatctgga tgg (58) | C1708T | R510X |

X: termination codon
[a] number in parenthesis shows SEQ ID NO.

(2) Introduction of Emp Gene Modification Plasmid into *B. choshinensis* and Confirmation of Genetic Modification

*B. choshinensis* was transformed based on TAKARA *Brevibacillus* Expression system HB300. After transformation, colonies were formed in an MTNm 50 ppm plate. The colonies were inoculated into MTNm 50 ppm liquid medium and subcultured twice, diluted and colonies were formed in the MT plate.

Medium

MTNm plate

MT medium added with neomycin (50 ppm)

MT Medium glucose 10 g/L

Phytone peptone 10 g/L

Erlich bonito extract 5 g/L powder yeast extract S 2 g/L $FeSO_4 \cdot 7H_2O$ 10 mg/L $MnSO_4 \cdot 4H_2O$ 10 mg/L $ZnSO_4 \cdot 7H_2O$ 1 mg/L adjusted to pH 7.0

The colonies grown were cultured in the MT liquid medium, emp gene segments were amplified by PCR using the following primers, and the sequences thereof were analyzed. As a result, it could be confirmed that a modification corresponding to the introduction of stop codon could be confirmed.

PCR primer F gggacatgattcgccggttg (SEQ ID NO: 59)

PCR primer R gcgtccatcgtagtaccagatc (SEQ ID NO: 60)

(3) Introduction of Other rmp Gene Modification Plasmid into *B. choshinensis* and Confirmation of Genetic Modification In addition, the other targeting sequences described in Table 7 were inserted into a targeting sequence insertion site of the modification CRISPR plasmid of the above-mentioned (1) to give a emp gene modification plasmid, and *B. choshinensis* was transformed by a method similar to that in the above-mentioned (2) to form a colony.

The colonies grown were cultured in the MT liquid medium, emp gene segments were amplified by PCR using the following primers, and the sequences thereof were analyzed. When the targeting sequence of No. 3 was used, a strain in which the 454th C was changed to T and glutamine was changed to stop codon could be obtained.

```
PCR primer F
                                   (SEQ ID NO: 74)
ccggaagccatacaggtaagatc PCR primer R
                                   (SEQ ID NO: 75)
cctgagtcgacatcaatcacgttc
```

From the above results, it was shown that the method of the present invention enables wide genetic modification of is gram-positive bacteria without accompanying insertion, deletion or DSB of the gene.

Example 4 Genetic Modification of *Clostridium saccharoperbutylacetonicum* (2)

(1) Production of Host for Destruction of Multiple Genes

Using 11757/ATCC27021, which is the 11757-carrying strain produced in Example 1(2), the DNA sequence of the pta gene of the ATCC27021 strain was converted. Then, for the production of a strain having multiple destroyed genes, plasmid 11757 was removed from the obtained mutation strain R311K (932nd base G of pta gene was modified to A) and G312R (934th base G of pta gene was modified to A).

Method

Using 11757/ATCC27021, which is the 11757-carrying strain produced in Example 1(2), conversion of DNA sequence and sequence analysis of the pta gene was performed by a method similar to that in Example 1(3). The mutation strain R311K (932nd base G of pta gene was modified to A) and G312R (934th base G of pta gene was modified to A) obtained as a result of the sequence analysis were cultured in a TYA medium free of antibiotics and dilution applied to a solid medium. Using the single colony grown therein as a template, the presence or absence of the plasmid retention was confirmed by the method shown in Example 1(2) and colonies free of an amplification product of the region peculiar to the plasmid were selected.

PCR composition (for one sample)

2×KODFX buffer 25 μL 2 mM dNTPS 10 μL

20 μM F primer 0.75 μL (NS-150410-i01)

20 μM R primer 0.75 μL (NS-150410-i02)

D.W. 11.5 μL

KODFX 1 μL

```
sequence of NS-150410-i01
                                   (SEQ ID NO: 61)
5'-CCGATAGOTAAGOCTATTGAG-3' sequence of NS-150410-i02
                                   (SEQ ID NO: 62)
5'-TCATCCTGTGGAGCTTAGTAG-3'
```

49 μL each was dispensed, a single colony suspension (1 μL) was added as the template, and PCR was performed under the following conditions.

94° C. 2 min

98° C. 10 sec→50° C. 30 sec→68° C. 2 min×30 cycles

10° C. hold

Results

The obtained PCR products were electrophoresed and colonies derived from respective mutated strain (R311K and G312R) and free of an amplification product of the region peculiar to the plasmid were used respectively used as 11757 fall off strains, ATCC 27021R311K and ATCC 27021G312R.

(2) Introduction of Vector Plasmid for Disruption into *C. saccharoperbutylacetonicum*

Four kinds of ptb1 vector plasmids for disruption 64G>A, 655G>A, 442C>T and 745G>A in which the targeting sequence portion [n20 portion (nucleotide No. 5560-5579) of the nucleotide sequence shown in SEQ ID NO: 4; corresponding to "Target" in the FIGURE] of the vector plasmid for disruption produced in Example 1(1) was substituted by a sequence complementary to each target nucleotide sequence in the ptb1 gene (SEQ ID NO: 63 and 64) of *C. saccharoperbutylacetonicum*, were constructed. The targeting sequences and the like of these vector plasmids for disruption are shown in Table 8.

TABLE 8

Outline of vector plasmids for disruption 64G > A, 442C > T, 655G > A, 745G > A

| vector for disruption | targeting sequence [a] (bold underline shows introduction site of mutation) | position of target nucleotide sequence in ptb1 gene | main position of mutation introduction |
|---|---|---|---|
| 64G > A | gccactgccactttctttgt (65) | 49-68 of ptb1[b] | 64G > A, 66G > A, 67G > A |
| 442C > T | ccagaattaaaggataaagt (66) | 442-461 of ptb1 | 442C > T, 443C > T |
| 655G > A | attgcattatctaaagcaaa (67) | 640-659 of ptb1 | 655G > A |
| 745G > A | acatttgctgtttctatatt (68) | 733-752 of ptb1 | 745G > A, 751G > A |

[a] number in parenthesis shows SEQ ID NO.
[b] see SEQ ID NO: 63 for nucleotide sequence of ptb1 gene In 64G>A, mutation of 64G>A and/or 66G>A and/or 67G>A was introduced into the target gene ptb1, and mutation of V22I or V22 and/or A23T was introduced at the amino acid level. 442C>T is a vector for disruption that mutates P148 to L or S. It is known that proline is an imino acid, which locally decreases the degree of freedom of protein. When it is changed to leucine, retention of the structure becomes difficult and reduction or loss of activity is expected. 655G>A is a vector for disruption that mutates A219 to T, 745G>A mutates A249 to T. Mutation of non-polar alanine having a small side chain to polar threonine having a bulky side chain changes the structure of PTB1 protein and is expected to reduce or eliminate the activity. 745G>A can also introduce mutation into 751G>A (V251 to I).

Method

*C. saccharoperbutylacetonicum* ATCC 27021 strain, and ATCC 27021R311K and ATCC 27021G312 strain produced in the above-mentioned (1) were transformed with the above-mentioned ptb1 vector plasmid for disruption 64G>A, 442C>T, 655G>A or 745G>A. Introduction of the vector plasmid for disruption and plasmid maintenance were confirmed by the method shown in Example 1(2).

Results

As a result of the plasmid maintenance confirmation PCR using the obtained strain as templates, amplification products in the region peculiar to the plasmid were obtained in all hosts, and they were confirmed to be transformants.

(3) *C. saccharoperbutylacetonicum* Ptb1 Gene Sequence Conversion Using Vector Plasmid for Disruption Using the vector plasmid for disruption, the DNA sequence of the ptb1 gene of butanol fermentation bacterium was converted. Since vector plasmid for disruption does not have a control mechanism in the destructive tool, it functions by simply forming generations.

Method

The 64G>A/ATCC 27021 strain as 64G>A-carrying strain, 442C>T/ATCC 27021 strain, 442C>T/ATCC 27021R311K strain and 442C>T/ATCC 27021G312 strain as 64G>A/ATCC 27021R312K strain and 64G>A/ATCC 27021G312 strain, 442C>T-carrying strain, 655G>A/ATCC 27021 strain as 655G>A-carrying strain, and 745G>A/ATCC 27021 strain, 745G>A/ATCC 27021R311K strain and 745G>A/ATCC 27021G312R strain as 655G>A/ATCC 27021R311K strain and 655G>A/ATCC 27021G312R strain, 745G>A-carrying strain, which were produced in the above-mentioned (2), were inoculated and cultured in TYA medium containing erythromycin (10 ppm), and dilution applied to TYA solid medium containing erythromycin (10 ppm) to give a single colony. The single colonies were picked and, using them as the templates, the full-length ptb1 gene on the genome was amplified.

The PCR composition and conditions followed those in Example 1(3) except that the primers used were NS-150819-i01 and NS-150819-i02 for ptb1.

sequence of NS-150819-i01
(SEQ ID NO: 69)
5'-GCAAGAAATGAGCAAAAACTTTGACG-3' sequence of NS-150819-i02
(SEQ ID NO: 70)
5'-GCTGCAACTAATGCTGCTAAAGC-3'

Then, the PCR product was purified by Wizard (registered trade mark) SV Gel and PCR Clean-Up System, and a sequence reaction was performed using the purified product as the template.

The PCR composition and conditions followed those in Example 1(3) except that the primer used was NS-150819-i01 (SEQ ID NO: 69) for the 64G>A-carrying strain and NS-150324-i01 for others.

sequence of NS-150324-i01
(SEQ ID NO: 71)
5'-CTCTGACTGTGCAGTTAACC-3'

Results

As a result of the sequence analysis of the colonies derived from the 64G>A-carrying strain, a strain showing introduction of mutation of 64G>A and/or 67G>A in the ptb1 gene was obtained. A strain that became V22I and/or A23T as PTB1 protein by the mutation of 64G>A and/or 67G>A was obtained. a strain showing introduction of V22M mutation was not found in the analysis at this time. As a result of the sequence analysis of the colonies derived from the 442C>T-carrying strain, a strain showing introduction of mutation into 442C>T and/or 443C>T was obtained. By the mutation of 442C>T and/or 443C>T, a strain having P148L or P148S as PTB1 protein was obtained. As a result of the sequence analysis of the colonies derived from the 655G>A-carrying strain was obtained. By the mutation of 655G>A, a strain having A219T as PTB1 protein was obtained. As a result of the sequence analysis of the colonies derived from the 745G>A-carrying strain, a strain showing introduction of mutation into 745G>A and/or 751G>A was obtained. By the mutation of 745G>A and/or 751G>A, a strain having A249T and/or V251I as PTB1 protein was obtained.

INDUSTRIAL APPLICABILITY

The present invention makes it possible to safely introduce site specific mutation into any gram-positive bacteria without accompanying insertion of a foreign DNA or double-stranded DNA breaks. Since the thus-obtained genetically modified strain is considered to not fall under a gene recombinant microorganism, reduction of the facility costs and waste disposal cost can be expected in industrial fermentative production using gram-positive bacteria, and the strain is extremely useful in that it enables reduction of the production costs.

This application is based on a patent application No. 2015-178022 filed in Japan (filing date: Sep. 9, 2015), the contents of which are incorporated in full herein.

The invention claimed is:

1. A method of modifying a targeted site in a double stranded DNA of a gram-positive bacterium, comprising a step of contacting a complex wherein a nucleic acid sequence-recognizing module that specifically binds to a target nucleotide sequence in a given double stranded DNA and a deaminase are bonded, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site, wherein the double stranded DNA is contacted with the complex by introducing the nucleic acid encoding the complex into the gram-positive bacterium, and wherein the gram-positive bacterium is a microorganism other than of the genus *Bacillus*.

2. The method according to claim 1, wherein said nucleic acid sequence-recognizing module is selected from the group consisting of a CRISPR-Cas system wherein at least one DNA cleavage ability of Cas is inactivated, a zinc finger motif, a TAL effector and a PPR motif.

3. The method according to claim 1, wherein said nucleic acid sequence-recognizing module is a CRISPR-Cas system wherein at least one DNA cleavage ability of Cas is inactivated.

4. The method according to claim 1, which uses two or more kinds of nucleic acid sequence-recognizing modules respectively specifically binding to different target nucleotide sequences.

5. The method according to claim 4, wherein said different target nucleotide sequence is present in a different gene.

6. The method according to claim 1, wherein said deaminase is cytidine deaminase.

7. The method according to claim 1, wherein said gram-positive bacterium is a microorganism belonging to the genus *Clostridium*, the genus *Brevibacillus* or the genus *Corynebacterium*.

8. The method according to claim 7, wherein the microorganism belonging to the genus *Clostridium* is *Clostridium saccharoperbutylacetonicum*.

9. The method according to claim 7, wherein the microorganism belonging to the genus *Brevibacillus* is *Brevibacillus choshinensis*.

10. The method according to claim 7, wherein the microorganism belonging to the genus *Corynebacterium* is *Corynebacterium glutamicum*.

11. The method according to claim 1, comprising a step of introducing an expression vector comprising a nucleic acid encoding said complex in a form permitting control of an expression period into said gram-positive bacterium, and a step of inducing expression of the nucleic acid for a period necessary for fixing the modification of the targeted site in the double stranded DNA.

12. The method according to claim 6, wherein said cytidine deaminase is PmCDA1.

* * * * *